United States Patent
Tada et al.

(10) Patent No.: US 9,142,785 B2
(45) Date of Patent: Sep. 22, 2015

(54) ORGANIC ELECTROLUMINESCENT ELEMENT

(75) Inventors: Masashi Tada, Kitakyushu (JP); Takahiro Kai, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 24 days.

(21) Appl. No.: 14/239,874

(22) PCT Filed: Aug. 6, 2012

(86) PCT No.: PCT/JP2012/070007
§ 371 (c)(1),
(2), (4) Date: Feb. 20, 2014

(87) PCT Pub. No.: WO2013/038843
PCT Pub. Date: Mar. 21, 2013

(65) Prior Publication Data
US 2014/0203269 A1    Jul. 24, 2014

(30) Foreign Application Priority Data
Sep. 12, 2011 (JP) .................. 2011-198705

(51) Int. Cl.
| | |
|---|---|
| H01L 51/00 | (2006.01) |
| C09K 11/06 | (2006.01) |
| H05B 33/14 | (2006.01) |
| C07D 405/14 | (2006.01) |
| C07D 409/14 | (2006.01) |
| C07D 209/86 | (2006.01) |
| H01L 51/50 | (2006.01) |

(52) U.S. Cl.
CPC .......... *H01L 51/0072* (2013.01); *C07D 209/86* (2013.01); *C07D 405/14* (2013.01); *C07D 409/14* (2013.01); *C09K 11/06* (2013.01); *H01L 51/0073* (2013.01); *H01L 51/0074* (2013.01); *H05B 33/14* (2013.01);
(Continued)

(58) Field of Classification Search
CPC ............ H01L 51/0545; H01L 51/0036; H01L 51/0541; H01L 51/5012
USPC .......................................................... 257/40
See application file for complete search history.

(56) References Cited

U.S. PATENT DOCUMENTS

| | | |
|---|---|---|
| 2005/0175858 A1 | 8/2005 | Jung et al. |
| 2007/0104976 A1 | 5/2007 | Iwakuma et al. |

(Continued)

FOREIGN PATENT DOCUMENTS

| | | |
|---|---|---|
| JP | 2004-71500 A | 3/2004 |
| JP | 2012-49518 A | 3/2012 |
| WO | WO-2010/079051 A1 | 7/2010 |

OTHER PUBLICATIONS

International Search Report for the Application No. PCT/JP2012/070007 mailed Oct. 16, 2012.
(Continued)

*Primary Examiner* — Monica D Harrison
(74) *Attorney, Agent, or Firm* — Cheng Law Group, PLLC

(57) ABSTRACT

Provided is an organic electroluminescent device (organic EL device) that is improved in luminous efficiency, sufficiently secures driving stability, and has a simple construction. The organic electroluminescent device includes an organic layer including a light-emitting layer between an anode and cathode laminated on a substrate, and at least one layer of the organic layer contains a carbazole compound represented by the following formula (1). It is advantageous to incorporate the carbazole compound as a host material into the light-emitting layer. In the formula (1), A represents a direct bond or an n-valent group, E represents oxygen or sulfur, and n represents an integer of 2 to 4.

5 Claims, 2 Drawing Sheets

(52) U.S. Cl.
CPC ............... *C09K 2211/1029* (2013.01); *C09K 2211/1088* (2013.01); *H01L 51/0085* (2013.01); *H01L 51/5016* (2013.01)

(56) References Cited

U.S. PATENT DOCUMENTS

2009/0017330 A1    1/2009    Iwakuma et al.
2011/0278552 A1*  11/2011  Numata et al. .............. 257/40

OTHER PUBLICATIONS

International Preliminary Report on Patentability (PCT/ISA/237 Written Opinion of the International Searching Authority) for the Application No. PCT/JP2012/070007 mailed Oct. 16, 2012 (English Translation dated Mar. 12, 2014).

* cited by examiner

ORGANIC ELECTROLUMINESCENT ELEMENT

TECHNICAL FIELD

The present invention relates to an organic electroluminescent device, and more specifically, to a thin-film type device that emits light by applying an electric field to a light-emitting layer formed of an organic compound.

BACKGROUND ART

In general, an organic electroluminescent device (hereinafter referred to as organic EL device) includes a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, optimization of kinds of electrodes has been attempted for the purpose of improving efficiency of injection of carriers from the electrodes. As a result, there has been developed a device in which a hole-transporting layer formed of an aromatic diamine and a light-emitting layer formed of an 8-hydroxyquinoline aluminum complex (hereinafter referred to as Alq3) are formed between electrodes as thin films, resulting in a significant improvement in luminous efficiency, as compared to conventional devices in which a single crystal of anthracene molecules or the like is used. Thus, development of the above-mentioned organic EL device has been promoted in order to accomplish its practical application to a high-performance flat panel having features such as self-luminescence and rapid response.

Further, studies have been made on using phosphorescent light rather than fluorescent light as an attempt to raise luminous efficiency of a device. Many kinds of devices including the above-mentioned device in which a hole-transporting layer formed of an aromatic diamine and a light-emitting layer formed of Alq3 are formed emit light by using fluorescent light emission. However, by using phosphorescent light emission, that is, by using light emission from a triplet excited state, luminous efficiency is expected to be improved by about three times to four times, as compared to the case of using conventional devices in which fluorescent light (singlet) is used. In order to accomplish this purpose, studies have been made on adopting a coumarin derivative or a benzophenone derivative as a light-emitting layer, but extremely low luminance has only been provided. Further, studies have been made on using a europium complex as an attempt to use a triplet state, but highly efficient light emission has not been accomplished. In recent years, many studies centered on an organic metal complex such as an iridium complex have been made, as disclosed in Patent Literature 1, for the purpose of attaining high luminous efficiency and a long lifetime.

CITATION LIST

Patent Literature

[PTL 1] WO 01/041512 A
[PTL 2] JP 2001-313178 A
[PTL 3] WO 2009/008100 A
[PTL 4] WO 2005/057987 A
[PTL 5] JP 2005-132820 A
[PTL 6] JP 2004-071500 A

In order to obtain high luminous efficiency, host materials that are used with the dopant materials described above play an important role. A typical example of the host material proposed is 4,4'-bis(9-carbazolyl)biphenyl (hereinafter referred to as CBP) as a carbazole compound introduced in Patent Literature 2. When CBP is used as a host material for a green phosphorescent light-emitting material typified by a tris(2-phenylpyridine) iridium complex (hereinafter referred to as Ir(ppy)3), the charge injection balance is disturbed because CBP has the characteristic of facilitating the delivery of holes and not facilitating the delivery of electrons. Thus, excessively delivered holes flow out into an electron-transporting layer side, with the result that the luminous efficiency from Ir(ppy) 3 lowers.

As described above, in order to provide high luminous efficiency to an organic EL device, it is necessary to use a host material that has high triplet excitation energy, and is striking a good balance in both charge (hole and electron)-injecting/transporting property. Further desired is a compound that has electrochemical stability, has high heat resistance, and has excellent amorphous stability, and hence further improvement has been demanded.

Patent Literature 3 discloses the carbazole compound shown below as a host material for an organic EL device.

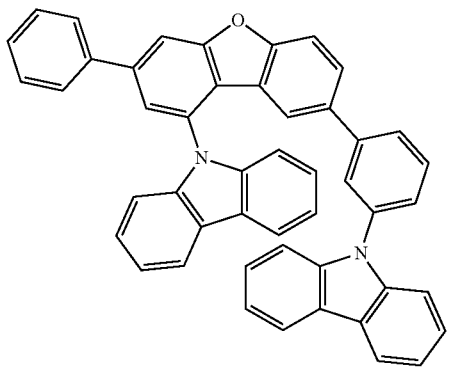 [SMILES: c1ccc(-c2cc(-n3c4ccccc4c4ccccc43)c3c(c2)oc2ccc(-c4cccc(-n5c6ccccc6c6ccccc65)c4)cc23)cc1]

However, it is assumed that the carbazole derivative does not provide sufficient luminous efficiency because the derivative has a phenyl group at each of the 3- and 7-positions of dibenzofuran.

Patent Literature 4 discloses the carbazole compound shown below as a host material for an organic EL device.

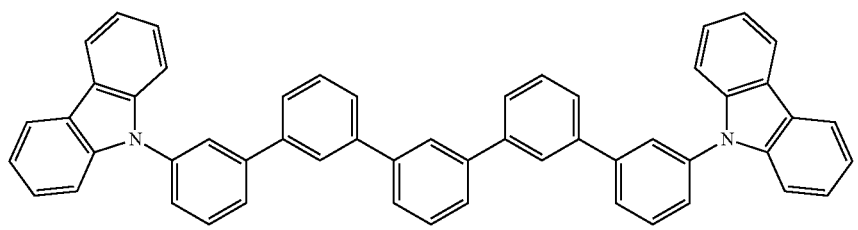 [SMILES: c1cc(-c2cccc(-c3cccc(-n4c5ccccc5c5ccccc54)c3)c2)cc(-c2cccc(-c3cccc(-n4c5ccccc5c5ccccc54)c3)c2)c1]

Patent Literature 5 discloses the carbazole compound shown below as a host material for an organic EL device.

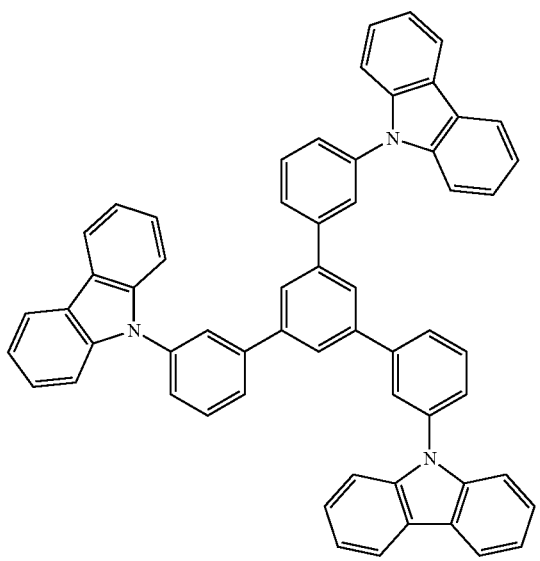 [SMILES: c1cc(-c2cc(-c3cccc(-n4c5ccccc5c5ccccc54)c3)cc(-c3cccc(-n4c5ccccc5c5ccccc54)c3)c2)cc(-n2c3ccccc3c3ccccc32)c1]

However, the disclosed compound is merely a compound in which carbazole is linked at its 9-position.

Patent Literature 6 discloses the carbazole compound shown below as a host material for an organic EL device.

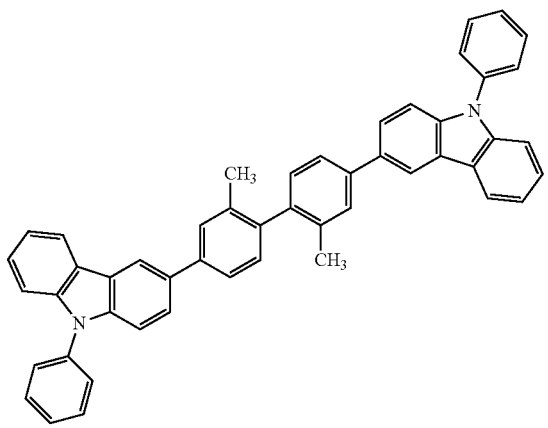 [SMILES: Cc1cc(-c2ccc3c(c2)c2ccccc2n3-c2ccccc2)ccc1-c1ccc(-c2ccc3c(c2)c2ccccc2n3-c2ccccc2)cc1C]

However, the disclosed compound is merely a compound obtained by introducing a phenyl group to the 9-position of carbazole, and the literature does not disclose the usefulness of an organic EL device using a compound obtained by introducing carbazole to the 1-position of dibenzothiophene or dibenzofuran.

SUMMARY OF INVENTION

In order that an organic EL device may be applied to a display device such as a flat panel display, the luminous efficiency of the device needs to be improved, and at the same time, its stability at the time of its driving needs to be sufficiently secured. The present invention has been made in view of the circumstances, and an object of the present invention is to provide an organic EL device that has high efficiency and high driving stability, and is hence practically useful, and a compound suitable for the device.

As a result of their extensive studies, the inventors of the present invention have found that the use of the following compound in an organic EL device causes the device to show excellent characteristics. The compound has a skeleton in which the N-position of carbazole is bonded to the 1-position of dibenzothiophene or dibenzofuran, and 2 to 4 skeletons of such type are linked at the 3-position of carbazole. Thus, the inventors have completed the present invention.

The present invention relates to an organic electroluminescent device, including: a substrate; an anode; an organic layer; and a cathode, the anode, the organic layer, and the cathode being laminated on the substrate, in which a carbazole compound represented by the general formula (1) is used in at least one layer selected from the group consisting of a light-emitting layer, a hole-transporting layer, an electron-transporting layer, a hole-blocking layer, and an election-blocking layer.

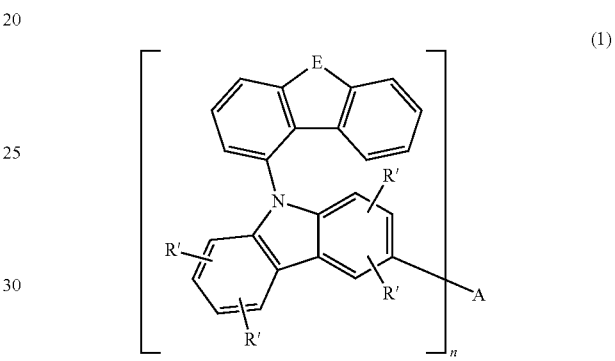

(1)

In the general formula (I):

A represents a direct bond, —O—, —S—, —Se—, >N—, >N—R, >Si—(R)$_2$, >Ge—(R)$_2$, an n-valent aliphatic hydrocarbon group having 1 to 12 carbon atoms, an n-valent alicyclic hydrocarbon group having 3 to 12 carbon atoms, an n-valent aromatic hydrocarbon group having 6 to 18 carbon atoms, an n-valent aromatic heterocyclic group having 3 to 17 carbon atoms, or an n-valent group obtained by linking 2 to 4 aromatic rings each selected from an aromatic hydrocarbon ring having 6 to 18 carbon atoms and an aromatic heterocycle having 3 to 17 carbon atoms, and the n-valent aromatic hydrocarbon group, the n-valent aromatic heterocyclic group, or the aromatic ring may have a substituent;

Rs each independently represent an alkyl group having 1 to 20 carbon atoms, a cycloalkyl group having 1 to 20 carbon atoms, an aromatic hydrocarbon group having 6 to 18 carbon atoms, or an aromatic heterocyclic group having 3 to 17 carbon atoms;

R's each independently represent hydrogen, an alkyl group having 1 to 12 carbon atoms, or an alkoxy group having 1 to 12 carbon atoms;

E represents oxygen or sulfur; and n represents an integer of 2 to 4.

In the general formula (1), it is preferred that A represent any one of a direct bond, an n-valent aliphatic hydrocarbon group having 1 to 6 carbon atoms, an n-valent alicyclic hydrocarbon group having 3 to 8 carbon atoms, the n-valent aromatic hydrocarbon group, the n-valent aromatic heterocyclic group, and the n-valent group obtained by linking 2 to 4 aromatic rings. In addition, it is more preferred that A represent any one of a direct bond, the n-valent aromatic hydrocarbon group, the n-valent aromatic heterocyclic group, and the n-valent group obtained by linking 2 to 4 aromatic rings.

In the general formula (1), it is preferred that n represent an integer of 2 or 3.

In addition, it is preferred that the organic electroluminescent device include a light-emitting layer containing the carbazole compound represented by the general formula (1) and a phosphorescent light-emitting dopant.

DESCRIPTION OF EMBODIMENTS

Figure 1:
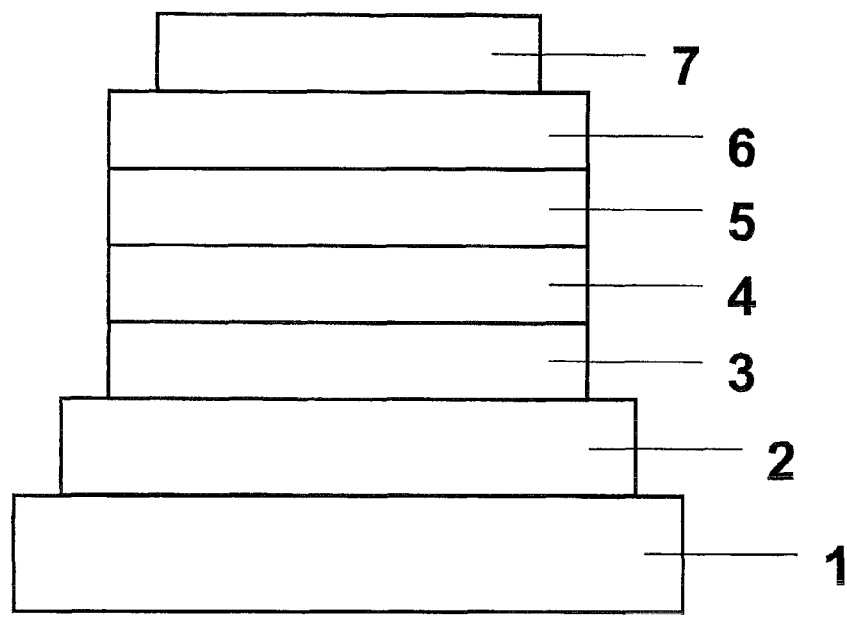
FIG. 1 is a sectional view illustrating a structural example of an organic EL device.

An organic electroluminescent device of the present invention contains a carbazole compound represented by the general formula (1) in a specific layer. In the general formula (1), A represents a direct bond or an n-valent group, and n represents 2, 3, or 4. A represents a direct bond, —O—, —S—, —Se—, >N—, >N—R, >Si—(R)$_2$, >Ge—(R)$_2$, an n-valent aliphatic hydrocarbon group having 1 to 12, preferably 1 to 6 carbon atoms, an n-valent alicyclic hydrocarbon group having 3 to 12, preferably 3 to 8 carbon atoms, an n-valent aromatic hydrocarbon group having 6 to 18 carbon atoms, an n-valent aromatic heterocyclic group having 3 to 17 carbon atoms, or an n-valent group obtained by linking 2 to 4 aromatic rings each selected from an aromatic hydrocarbon ring having 6 to 18 carbon atoms and an aromatic heterocycle having 3 to 17 carbon atoms.

Here, the n-valent aromatic hydrocarbon group, the n-valent aromatic heterocyclic group, the aromatic hydrocarbon ring, and the aromatic heterocycle may each have a substituent or may each be free of any substituent.

A preferably represents a direct bond, the n-valent aliphatic hydrocarbon group, the n-valent alicyclic hydrocarbon group, the n-valent aromatic hydrocarbon group, the n-valent aromatic heterocyclic group, or the n-valent group obtained by linking 2 to 4 aromatic rings.

When A represents an n-valent aliphatic hydrocarbon group having 1 to 12 carbon atoms, the group may be saturated or unsaturated, and may be linear or branched. Specific examples thereof include n-valent groups each obtained by removing n hydrogen atoms from a saturated or unsaturated aliphatic hydrocarbon such as methane, ethane, ethene, ethyne, propane, propene, propyne, butane, butene, butadiene, butyne, pentane, pentene, pentyne, hexane, heptane, octane, nonane, or decane. The group is preferably an n-valent aliphatic hydrocarbon group having 1 to 6 carbon atoms. The group is more preferably a divalent to tetravalent aliphatic hydrocarbon group produced by removing 2 to 4 hydrogen atoms from an aliphatic hydrocarbon represented by CmH2 m+2 where m represents 1 to 6.

When A represents an n-valent alicyclic hydrocarbon group having 3 to 12 carbon atoms, the group may be saturated or unsaturated, and may be branched. Specific examples thereof include n-valent groups each obtained by removing n hydrogen atoms from a saturated or unsaturated alicyclic hydrocarbon such as cyclopropane, cyclobutane, cyclobutene, cyclobutadiene, cyclopentane, cyclopentene, cyclohexane, methylcyclohexane, cycloheptane, or cyclooctane. The group is preferably an n-valent aliphatic hydrocarbon group having 3 to 8 carbon atoms. The group is more preferably a divalent to tetravalent aliphatic hydrocarbon group produced by removing 2 to 4 hydrogen atoms from an alicyclic hydrocarbon represented by CmH2 m+2 where m represents 3 to 8.

When A represents an n-valent aromatic hydrocarbon group having 6 to 18 carbon atoms or an n-valent aromatic heterocyclic group having 3 to 17 carbon atoms, specific examples of these groups include n-valent groups each produced by removing n hydrogen atoms from an aromatic compound selected from benzene, naphthalene, fluorene, anthracene, phenanthrene, fluoranthene, pyrene, chrysene, pyridine, pyrimidine, triazine, indole, quinoline, isoquinoline, quinoxaline, naphthyridine, carbazole, acridine, phenanthroline, phenazine, benzofuran, dibenzofuran, xanthene, oxanthrene, phenoxazine, benzothiophene, dibenzothiophene, thioxanthene, thianthrene, phenoxathiin, and phenothiazine. Of those, an n-valent group produced by removing n hydrogen atoms from an aromatic compound selected from the following compounds is preferred: benzene, naphthalene, fluorene, anthracene, phenanthrene, fluoranthene, pyrene, chrysene, pyridine, pyrimidine, triazine, indole, quinoline, isoquinoline, quinoxaline, naphthyridine, carbazole, acridine, benzofuran, dibenzofuran, phenoxazine, benzothiophene, dibenzothiophene, and phenothiazine. An n-valent group produced by removing n hydrogen atoms from an aromatic compound selected from the following compounds is more preferred: benzene, indole, pyridine, pyrimidine, triazine, carbazole, benzofuran, dibenzofuran, benzothiophene, and dibenzothiophene.

When A represents an n-valent group obtained by linking 2 to 4 aromatic rings each selected from an aromatic hydrocarbon ring having 6 to 18 carbon atoms and an aromatic heterocycle having 3 to 17 carbon atoms, examples of the aromatic hydrocarbon ring and the aromatic heterocycle include n-valent groups each produced by removing n hydrogen atoms from an aromatic compound produced by linking 2 to 4 aromatic compounds described for the case where A represents an n-valent aromatic hydrocarbon group having 6 to 18 carbon atoms or an n-valent aromatic heterocyclic group having 3 to 17 carbon atoms.

The aromatic compound that provides the aromatic ring is preferably benzene, naphthalene, fluorene, anthracene, phenanthrene, fluoranthene, pyrene, chrysene, pyridine, pyrimidine, triazine, indole, quinoline, isoquinoline, quinoxaline, naphthyridine, carbazole, acridine, benzofuran, dibenzofuran, phenoxazine, benzothiophene, dibenzothiophene, or, phenothiazine. The compound is more preferably benzene, indole, pyridine, pyrimidine, triazine, carbazole, benzofuran, dibenzofuran, benzothiophene, or dibenzothiophene.

Here, the aromatic hydrocarbon rings or aromatic heterocycles constituting the aromatic compound obtained by linking 2 to 4 aromatic rings may be identical to or different from each other, and the compound may contain both the aromatic hydrocarbon ring and the aromatic heterocycle. Specific examples of the aromatic compound obtained by linking 2 to 4 aromatic rings include n-valent groups each produced by removing n hydrogen atoms from biphenyl, terphenyl, bipyridine, bipyrimidine, bitriazine, bistriazylbenzene, binaphthalene, phenylpyridine, diphenylpyridine, diphenylpyrimidine, diphenyltriazine, phenylcarbazole, diphenylcarbazole, dicarbazolylbenzene, pyridylcarbazole, phenyldibenzofuran, phenyldibenzothiophene, or the like. A bonding position is not limited, and may be a terminal ring or a ring in a central moiety.

The aromatic hydrocarbon ring or the aromatic heterocycle can have a substituent as in the n-valent aromatic hydrocarbon group and the n-valent aromatic heterocyclic group. When the n-valent aromatic hydrocarbon group, the n-valent aromatic heterocyclic group, the aromatic hydrocarbon ring, or the aromatic heterocycle has a substituent, the substituent is preferably, for example, an alkyl group having 1 to 12 carbon atoms, a cycloalkyl group having 3 to 12 carbon atoms, an alkoxy group having 1 to 12 carbon atoms, an acyl group having 2 to 13 carbon atoms, or a diarylamino group having 12 to 24 carbon atoms. Of those, an alkyl group having 1 to 6 carbon atoms, a cycloalkyl group having 3 to 8 carbon atoms, an alkoxy group having 1 to 6 carbon atoms, an acyl group having 2 to 7 carbon atoms, or a diarylamino group having 12 to 20 carbon atoms is preferred. When such group or ring has a substituent, the total number of substituents is 1 to 10, preferably 1 to 6, more preferably 1 to 4. In addition, when the aromatic hydrocarbon group, the aromatic heterocyclic group, or the aromatic ring has 2 or more substituents, the substituents may be identical to or different from each other. In addition, in the calculation of the number of carbon atoms of the aromatic hydrocarbon group, the aromatic heterocyclic group, or the aromatic ring, when such group or ring has a substituent, the number of carbon atoms of the substituent is not included. When the aromatic hydrocarbon group, the aromatic heterocyclic group, or the aromatic ring is a substituted aromatic hydrocarbon group, a substituted aromatic heterocyclic group, or a substituted aromatic ring, in the case of a substituted aromatic hydrocarbon group or a substituted aromatic hydrocarbon ring, the total number of carbon atoms of such group or ring is preferably 6 to 50, more preferably 6 to 30. In the case of a substituted aromatic heterocyclic group or a substituted aromatic heterocycle, the total number of carbon atoms of such group or ring is preferably 3 to 50, more preferably 4 to 30.

Here, the n-valent group produced from the aromatic compound obtained by linking 2 to 4 aromatic rings is represented by, for example, any one of the following formulae when the group is a divalent group.

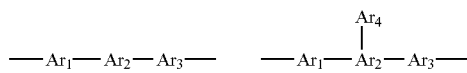

(Ar$_1$ to Ar$_4$ each represent an aromatic ring.)

When A represents >N—R, >Si—(R)$_2$, or >Ge—(R)$_2$, Rs each independently represent an alkyl group having 1 to 20 carbon atoms, a cycloalkyl group having 1 to 20 carbon atoms, an aromatic hydrocarbon group having 6 to 18 carbon atoms, or an aromatic heterocyclic group having 3 to 17 carbon atoms, preferably an alkyl group having 1 to 12 carbon atoms, a cycloalkyl group having 1 to 12 carbon atoms, an aromatic hydrocarbon group having 6 to 12 carbon atoms, or an aromatic heterocyclic group having 3 to 12 carbon atoms.

Specific examples of the alkyl group or cycloalkyl group having 1 to 20 carbon atoms include a methyl group, an ethyl group, a propyl group, a butyl group, a hexyl group, a heptyl group, an octyl group, a nonyl group, a decyl group, a cyclohexyl group, and a methylcyclohexyl group, and the group may be linear or branched. Of those, a methyl group, an ethyl group, a propyl group, a butyl group, a pentyl group, a hexyl group, or a cyclohexyl group is preferred.

Specific examples of the aromatic hydrocarbon group having 6 to 18 carbon atoms or the aromatic heterocyclic group having 3 to 17 carbon atoms include groups each produced by removing hydrogen from benzene, naphthalene, fluorene, anthracene, phenanthrene, fluoranthene, pyrene, chrysene, pyridine, pyrimidine, triazine, indole, quinoline, isoquinoline, quinoxaline, naphthyridine, carbazole, acridine, phenanthroline, phenazine, benzofuran, dibenzofuran, xanthene, oxanthrene, phenoxazine, benzothiophene, dibenzothiophene, thioxanthene, thianthrene, phenoxathiin, phenothiazine, or the like. Of those, a group produced by removing hydrogen from the following compounds is preferred: benzene, naphthalene, fluorene, anthracene, phenanthrene, fluoranthene, pyrene, chrysene, pyridine, pyrimidine, triazine, indole, quinoline, isoquinoline, quinoxaline, naphthyridine, carbazole, acridine, benzofuran, dibenzofuran, phenoxazine, benzothiophene, dibenzothiophene, phenothiazine, and the like. A group obtained by removing hydrogen from the following compounds is more preferred: benzene, naphthalene, anthracene, phenanthrene, pyridine, pyrimidine, triazine, and quinoline.

In the general formula (1), R's each independently represent hydrogen, an alkyl group having 1 to 12 carbon atoms, or an alkoxy group having 1 to 12 carbon atoms, preferably hydrogen, an alkyl group having 1 to 6 carbon atoms, or an alkoxy group having 1 to 6 carbon atoms. Specific examples of the alkyl group or the alkoxy group include a methyl group, an ethyl group, a propyl group, a butyl group, a hexyl group, a heptyl group, an octyl group, a nonyl group, a decyl group, a methoxy group, an ethoxy group, a propoxy group, and a butoxy group, and the alkyl chain may be linear or branched. Of those, a methyl group, an ethyl group, a propyl group, a butyl group, a pentyl group, a hexyl group, a methoxy group, an ethoxy group, a propoxy group, or a butoxy group is preferred.

In the general formula (1), E represents oxygen or sulfur, and n represents an integer of 2 to 4, preferably 2 or 3.

Out of the skeletons represented by the general formula (1), a skeleton in which E is represented by O can be synthesized by the following reaction formulae with reference to a synthesis example described in WO 2009-145016 A1.

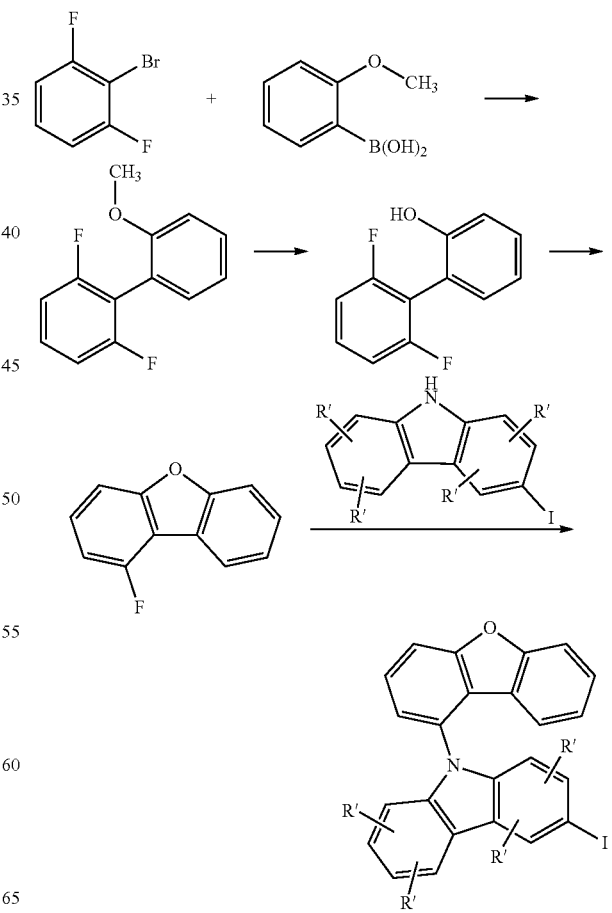

In addition, a skeleton in which E is represented by S can be synthesized by the following reaction formulae.

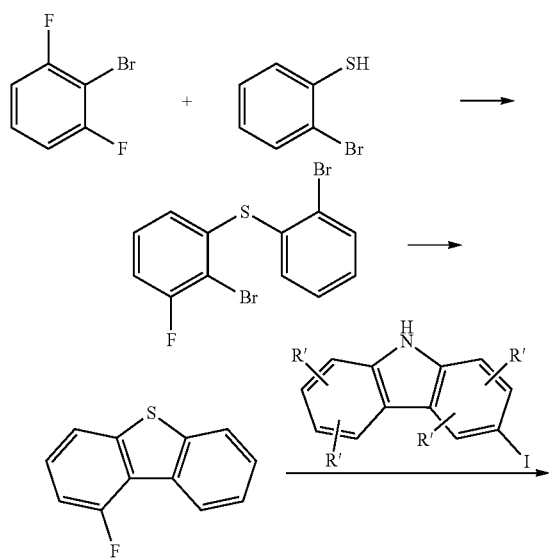

The compound represented by the general formula (1) can be synthesized by substituting iodine of any of the various compounds obtained by the foregoing reaction formulae with the corresponding linking group through a coupling reaction such as Suzuki coupling.

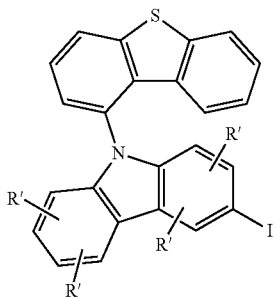

Specific examples of the compound represented by the general formula (1) are shown below. However, the compound is not limited to the exemplified compounds.

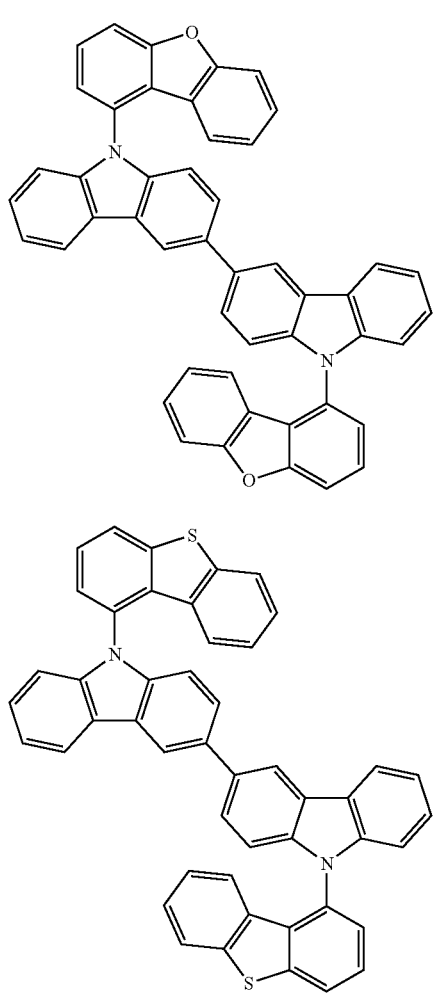

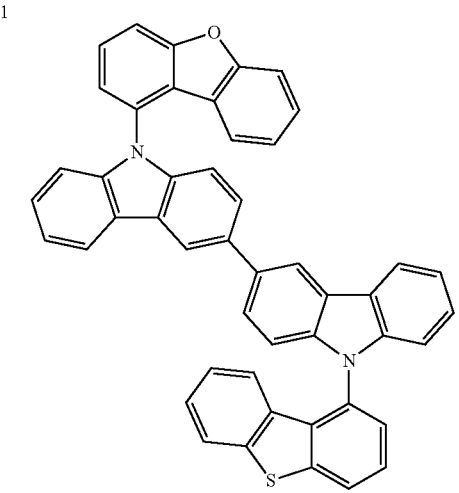

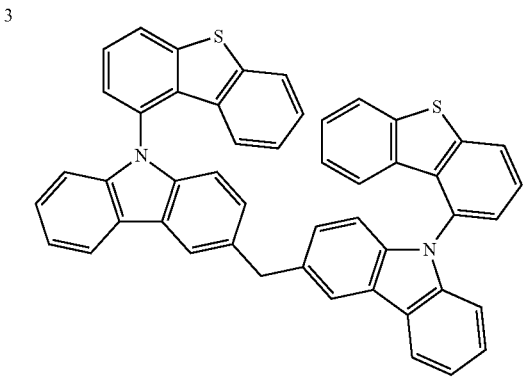

-continued
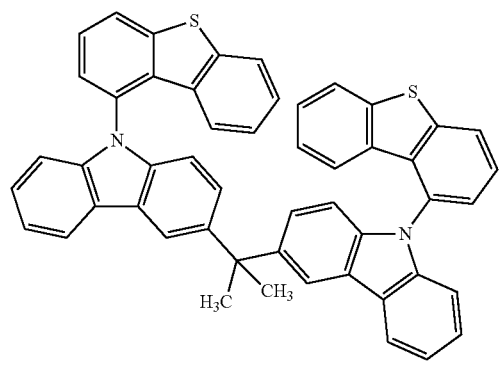
5
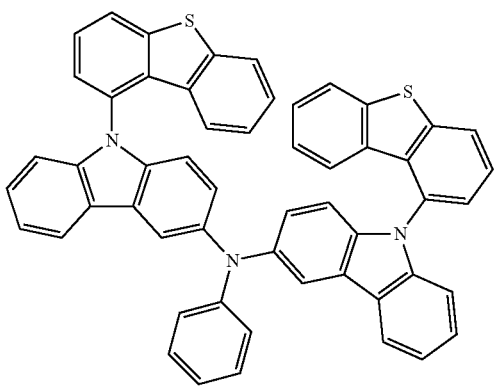
6
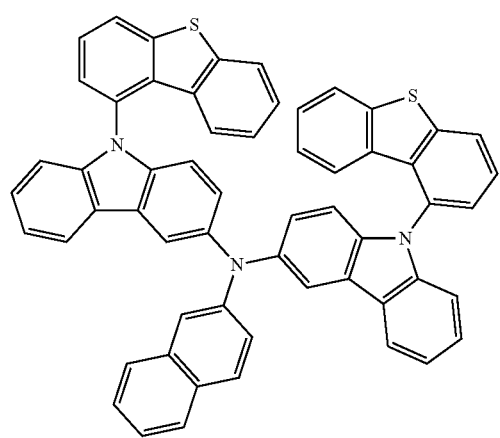
7
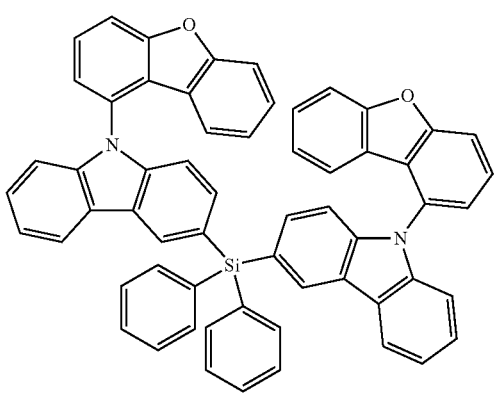
8
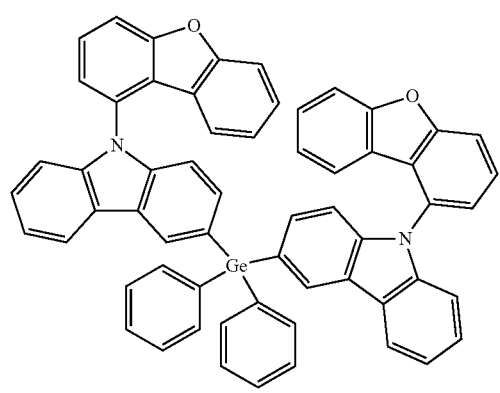
9
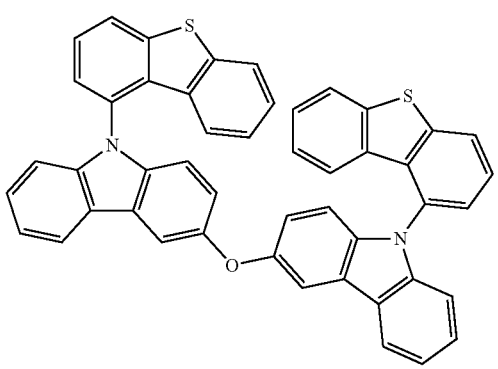
10

11
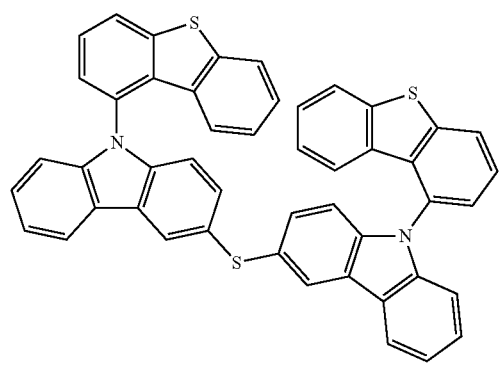
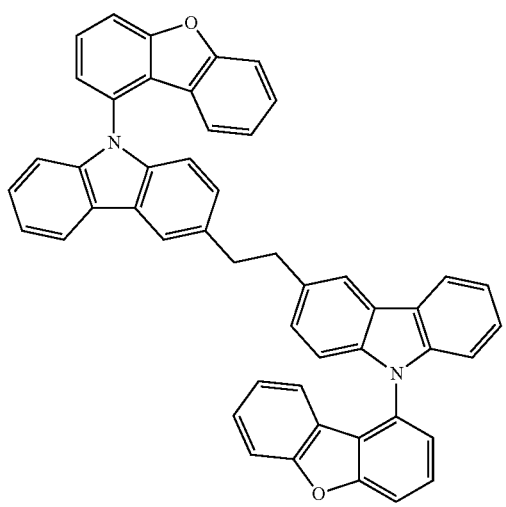
12
13
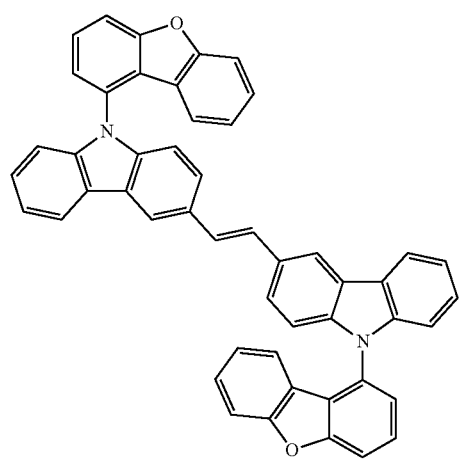
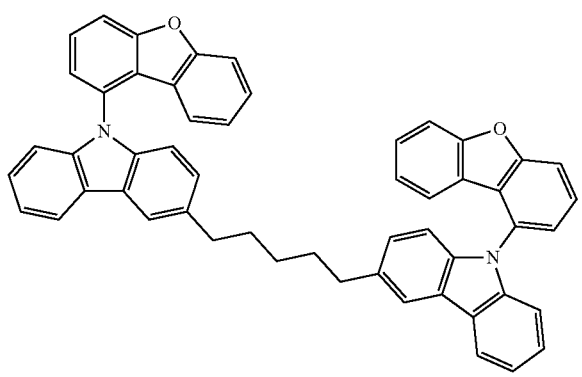
14
15
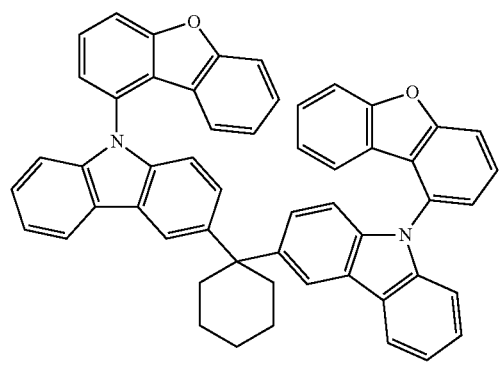
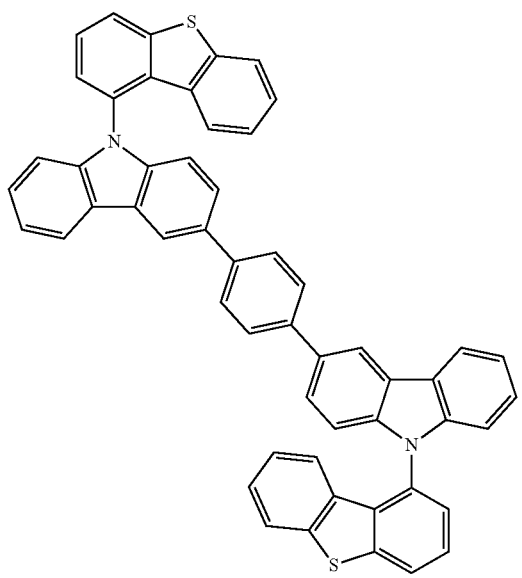
16

-continued
17
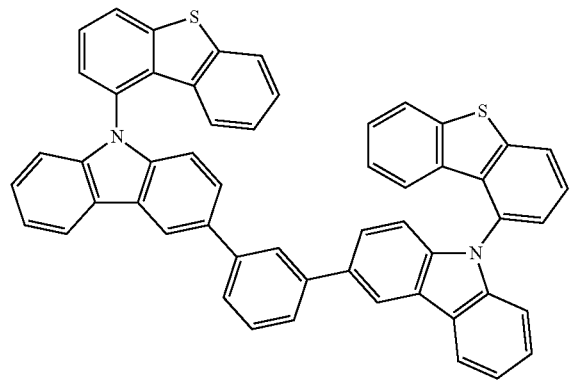
18
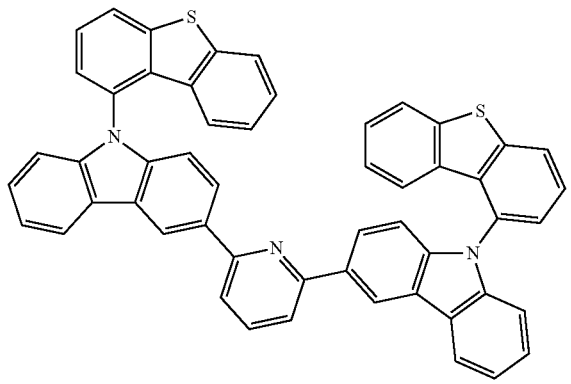
19
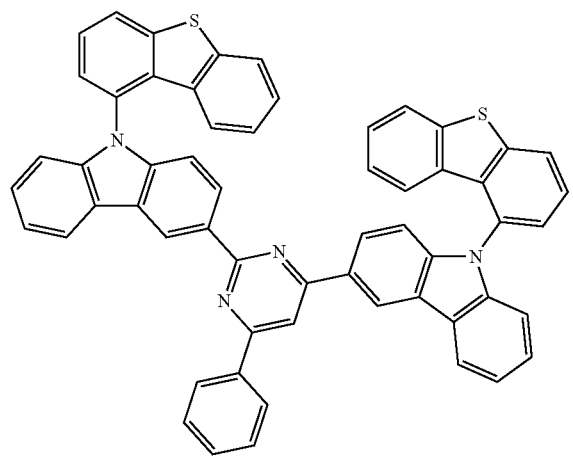
20
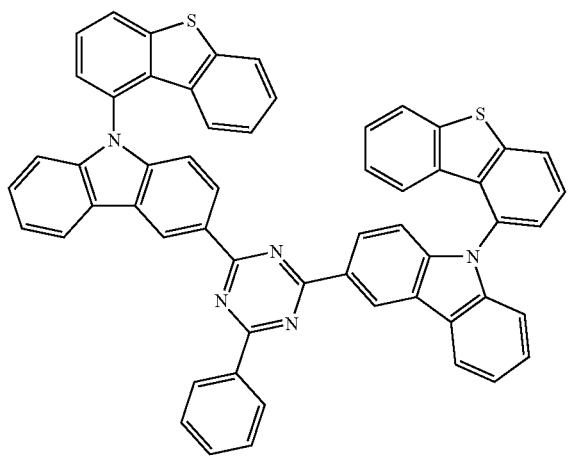
21
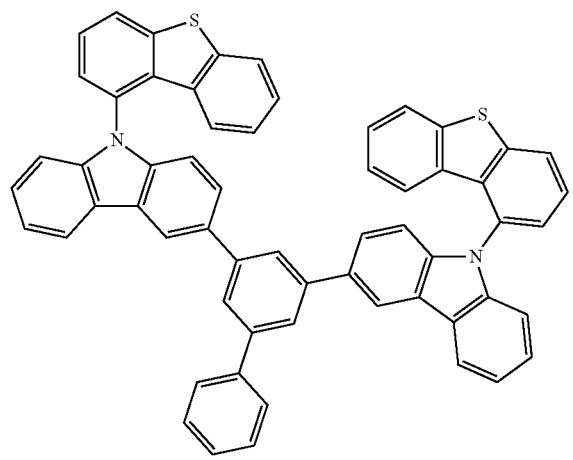
22
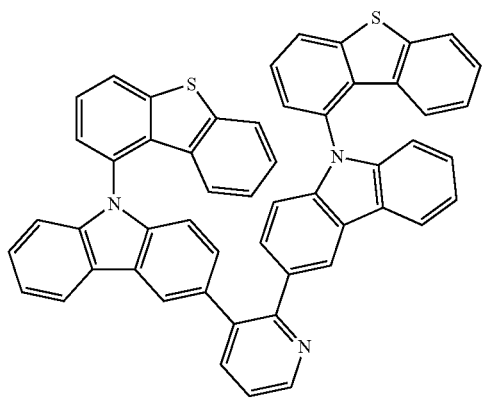

-continued
23
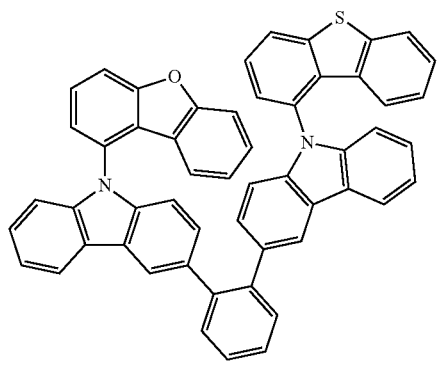
24
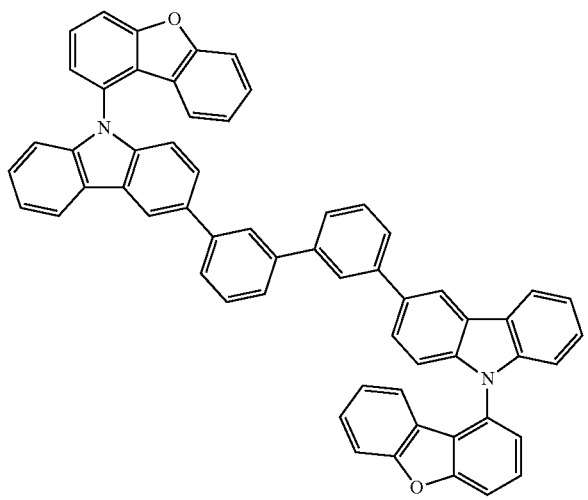
25
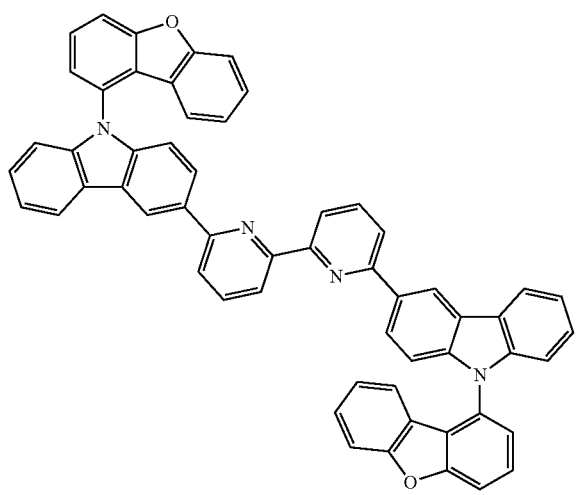
26
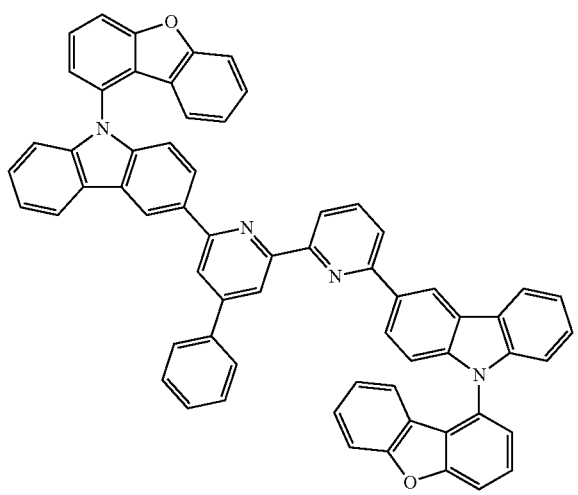
27
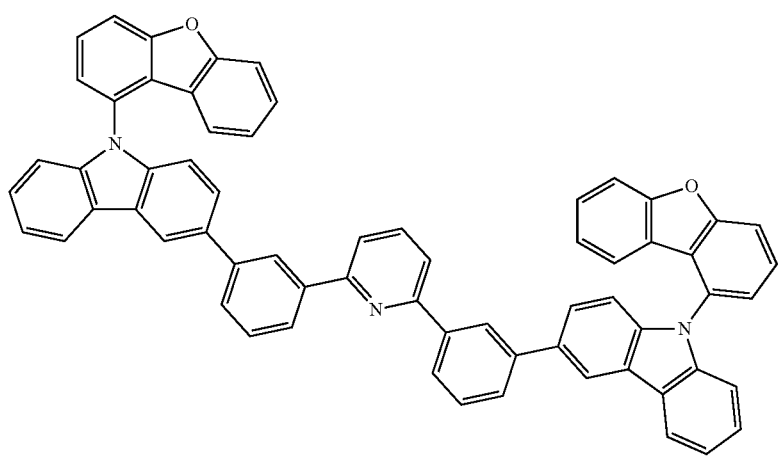

-continued
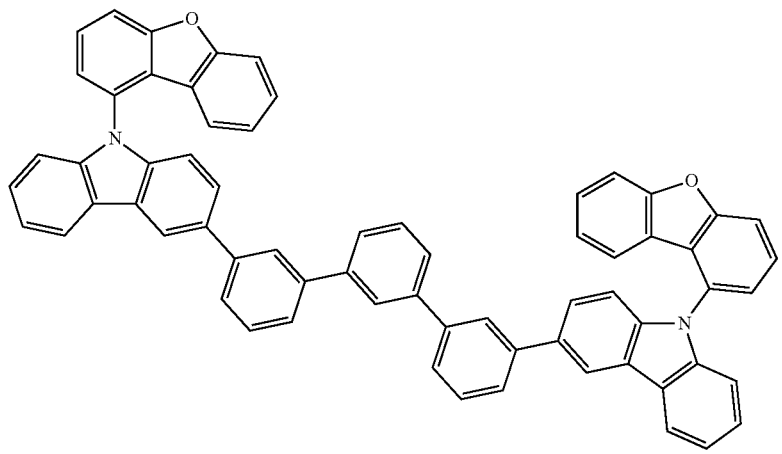
28
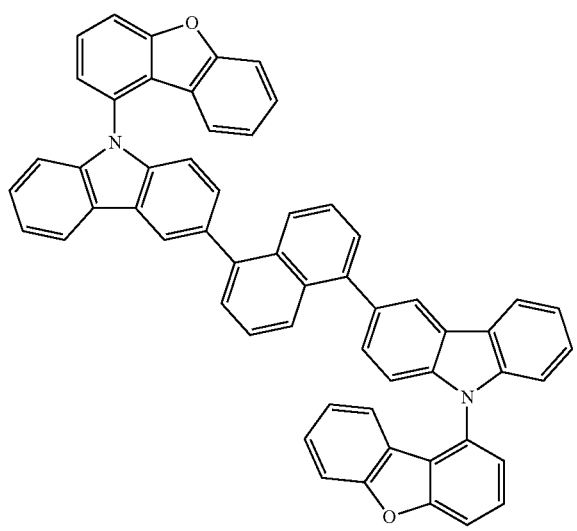
29
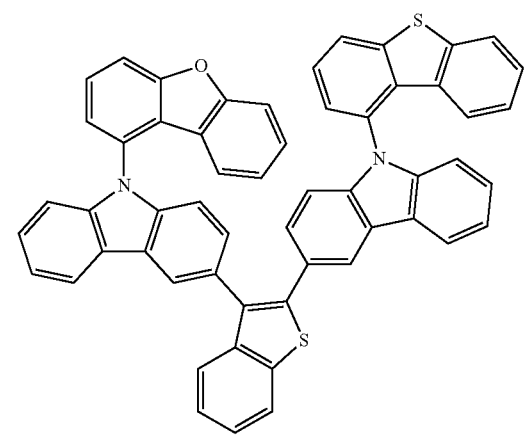
30
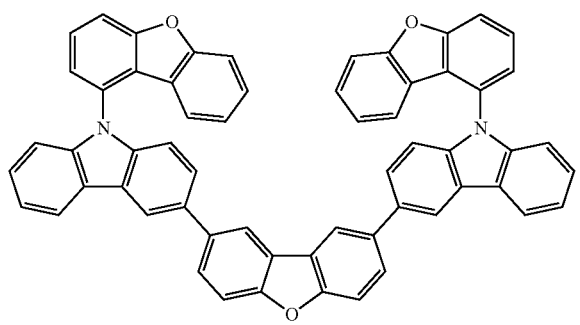
31
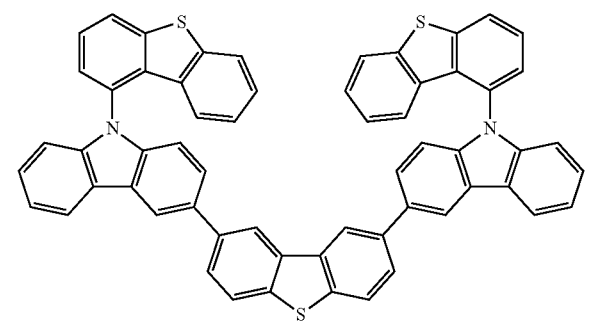
32

-continued
33
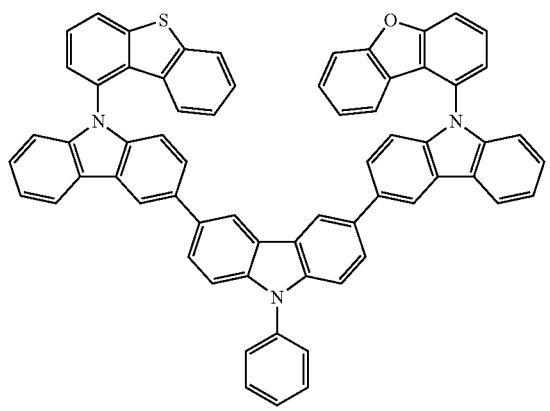
34
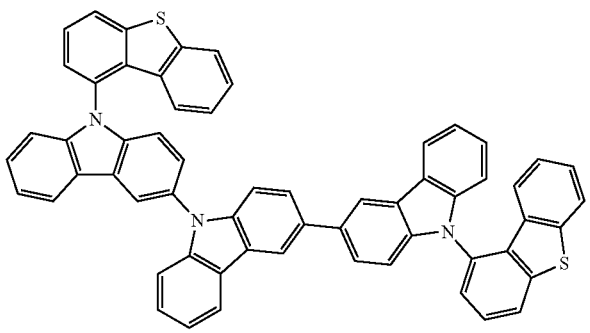
35
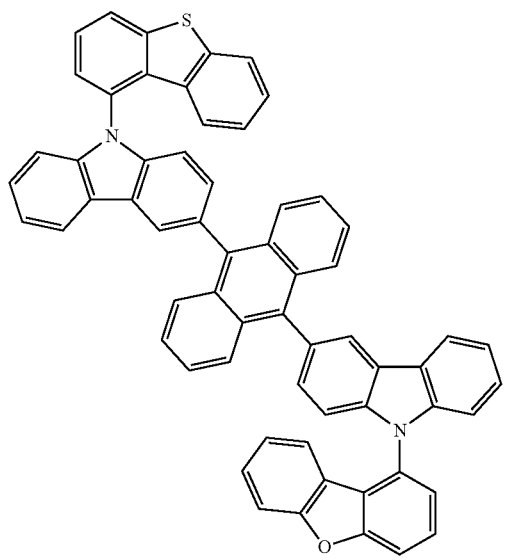
35
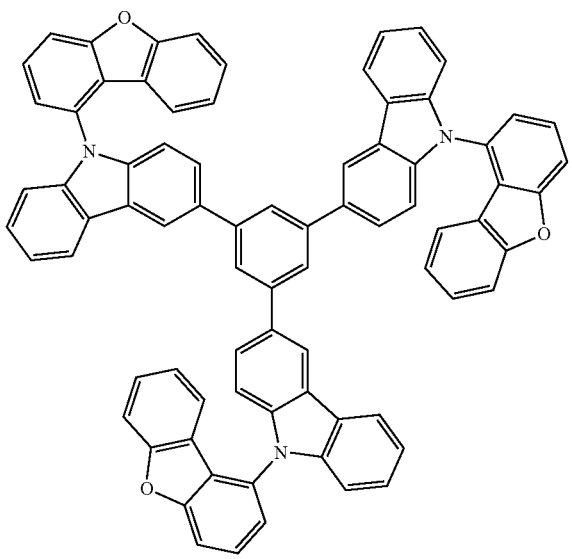
36
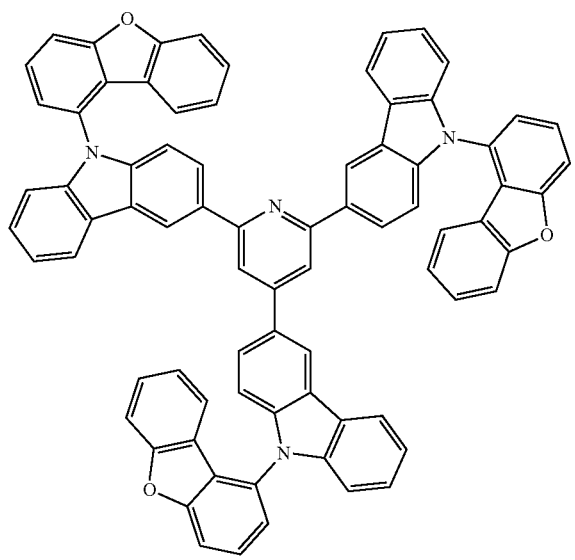
37
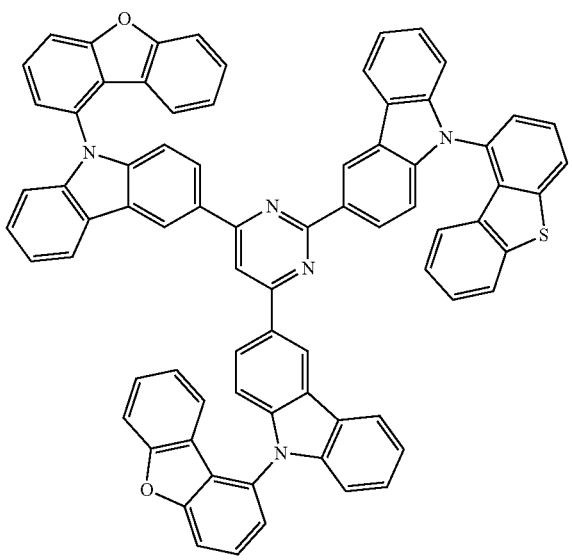

-continued

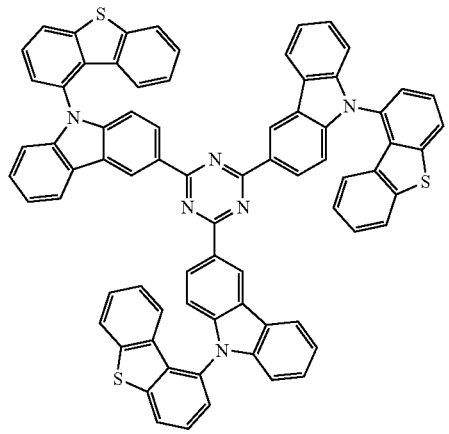
38

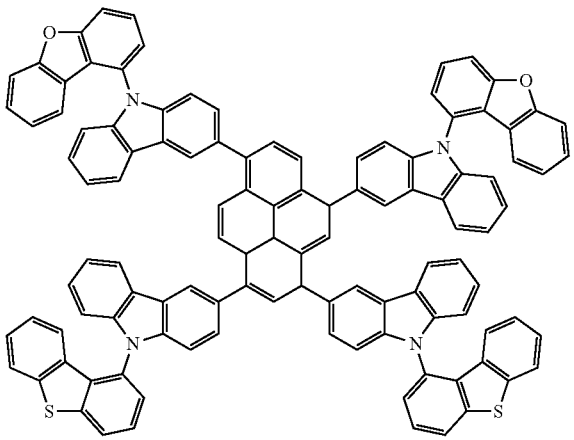
39

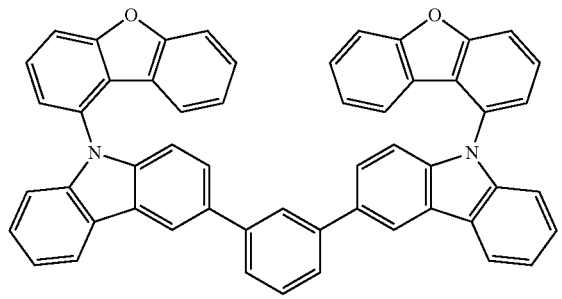
40

When the carbazole compound represented by the general formula (1) is incorporated into at least one organic layer in an organic EL device formed by laminating an anode, a plurality of organic layers, and a cathode on a substrate, an excellent organic electroluminescent device is provided. A light-emitting layer, a hole-transporting layer, an electron-transporting layer, or a hole-blocking layer is suitable as the organic layer into which the carbazole compound is incorporated. It is more preferred that the carbazole compound be incorporated as a host material in a light-emitting layer containing a phosphorescent light-emitting dopant.

Next, the organic EL device of the present invention is described.

The organic EL device of the present invention includes organic layers including at least one light-emitting layer between an anode and a cathode laminated on a substrate. In addition, at least one of the organic layers contains the carbazole compound. The carbazole compound represented by the general formula (1) is advantageously contained in the light-emitting layer together with a phosphorescent light-emitting dopant.

Next, the structure of the organic EL device of the present invention is described with reference to the drawings. However, the structure of the organic EL device of the present invention is by no means limited to one illustrated in the drawings.

FIG. 1 is a sectional view illustrating a structural example of a general organic EL device. Reference numerals 1, 2, 3, 4, 5, 6, and 7 represent a substrate, an anode, a hole-injecting layer, a hole-transport layer, a light-emitting layer, an electron-transport layer, and a cathode, respectively. The organic EL device of the present invention may include an exciton-blocking layer adjacent to the light-emitting layer, or may include an electron-blocking layer between the light-emitting layer and the hole-injecting layer. The exciton-blocking layer may be inserted on any of the anode side and the cathode side of the light-emitting layer, and may also be inserted simultaneously on both sides. The organic EL device of the present invention includes the substrate, the anode, the light-emitting layer, and the cathode as its essential layers. The organic EL device of the present invention preferably includes a hole-injecting/transporting layer and an electron-injecting/transporting layer in addition to the essential layers, and more preferably includes a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure compared with FIG. 1, that is, a structure formed by laminating the layers on the substrate 1 in the order of the cathode 7, the electron-transporting layer 6, the light-emitting layer 5, the hole-transporting layer 4, and the anode 2. In this case as well, a layer may be added or eliminated as required.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which may be used for manufacturing an amorphous, transparent conductive film. In order to produce the anode, it may be possible to form any of those electrode substances into a thin film by using a method such as vapor deposition or sputtering and form a pattern having a desired shape thereon by photolithography. Alternatively, in the case of not requiring high pattern accuracy (about 100 μm or more), a pattern may be formed via a mask having a desired shape when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. Further, the sheet resistance as the anode is preferably several hundred Ω/□ or less. Further, the thickness of the resultant film is, depending on the material used, selected from usually the range of 10 to 1,000 nm, preferably the range of 10 to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode may be produced by forming any of those electrode substances into a thin film by using a method such as vapor deposition or sputtering. Further, the sheet resistance as the cathode is preferably several hundred Ω/□ or less, and the thickness of the resultant film is selected from usually the range of 10 nm to 5 μm, preferably the range of 50 to 200 nm. It should be noted that, in order for luminescence produced to pass through, any one of the anode and cathode of the organic EL device is preferably transparent or semi-transparent, because the light emission luminance improves.

Further, after any of the above-mentioned metals is formed into a film having a thickness of 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Light-Emitting Layer—

The light-emitting layer is a phosphorescent light-emitting layer, and contains a phosphorescent light-emitting dopant and a host material. It is recommended to use, as a material for the phosphorescent light-emitting dopant, a material containing an organic metal complex including at least one metal selected from ruthenium, rhodium, palladium, silver, rhenium, osmium, iridium, platinum, and gold. Specific examples thereof include, but not limited to, compounds described in the following patent publications. The numbers of the patent publications and the like are described below.

For example, WO 2009/073245 A1, WO 2009/046266 A1, WO 2007/095118 A3, WO 2008/156879 A1, WO 2008/140657 A1, US 2008/261076 A, JP 2008-542203 A, WO 2008/054584 A1, JP 2008-505925 A, JP 2007-522126 A, JP 2004-506305 A, JP 2006-513278 A, JP 2006-50596 A, WO 2006/046980 A1, WO 2005/113704 A3, US 2005/260449 A, US 2005/2260448 A, US 2005/214576 A, WO 2005/076380 A3, US 2005/119485 A, WO 2004/045001 A3, WO 2004/045000 A3, WO 2006/100888 A1, WO 2007/004380 A1, WO 2007/023659 A1, WO 2008/035664 A1, JP 2003-272861 A, JP 2004-111193 A, JP 2004-319438 A, JP 2007-2080 A, JP 2007-9009 A, JP 2007-227948 A, JP 2008-91906 A, JP 2008-311607 A, JP 2009-19121 A, JP 2009-46601 A, JP 2009-114369 A, JP2003-253128 A, JP 2003-253129 A, JP 2003-253145 A, JP 2005-38847 A, JP 2005-82598 A, JP 2005-139185 A, JP 2005-187473 A, JP 2005-220136 A, JP 2006-63080 A, JP2006-104201 A, JP2006-111623 A, JP2006-213720 A, JP2006-290891 A, JP2006-298899 A, JP 2006-298900 A, WO 2007/018067 A1, WO 2007/058080 A1, WO 2007/058104 A1, JP 2006-131561 A, JP 2008-239565 A, JP 2008-266163 A, JP 2009-57367 A, JP 2002-117978 A, JP 2003-123982 A, JP 2003-133074 A, JP 2006-93542 A, JP2006-131524 A, JP 2006-261623 A, JP 2006-303383 A, JP2006-303394 A, JP 2006-310479 A, JP 2007-88105 A, JP 2007-258550 A, JP2007-324309 A, JP 2008-270737 A, JP2009-96800 A, JP 2009-161524 A, WO 2008/050733A1, JP 2003-73387 A, JP2004-59433 A, JP 2004-155709 A, JP 2006-104132 A, JP 2008-37848 A, JP 2008-133212 A, JP 2009-57304 A, JP 2009-286716 A, JP 2010-83852 A, JP2009-532546 A, JP 2009-536681 A, and JP 2009-542026 A.

Preferred examples of the phosphorescent light-emitting dopant include complexes such as Ir(ppy) 3, complexes such as Ir(bt) 2.acac3, and complexes such as PtOEt3, the complexes each having a noble metal element such as Ir as a central metal. Specific examples of those complexes are shown below, but the complexes are not limited to the compounds described below.

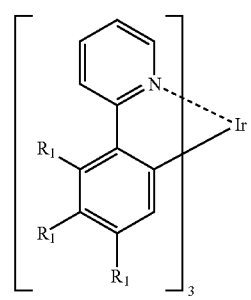

R1: H, CH3, CF3, F

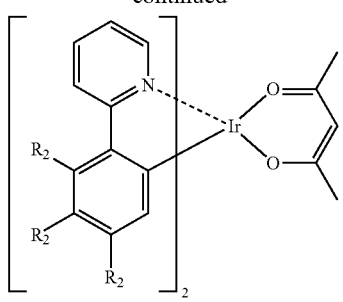
R2: H, F
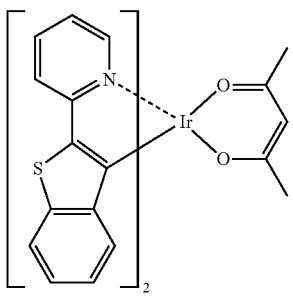
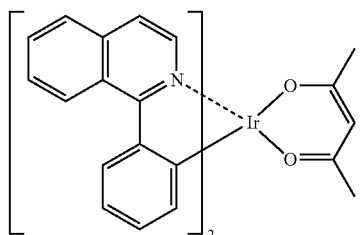
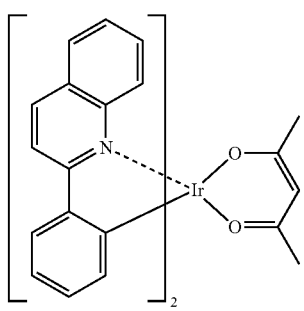 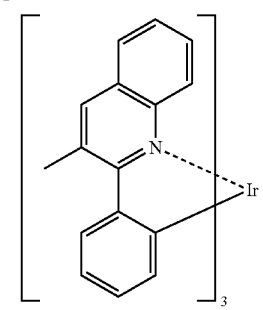
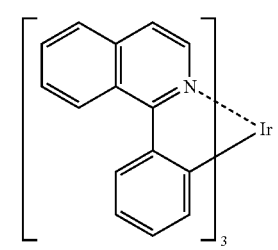
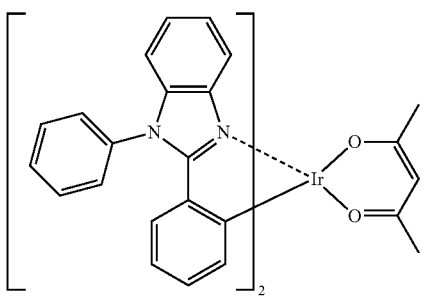
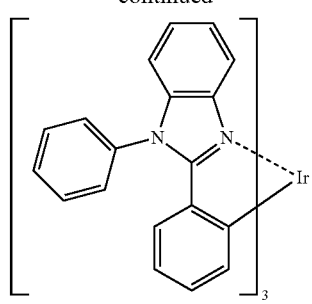
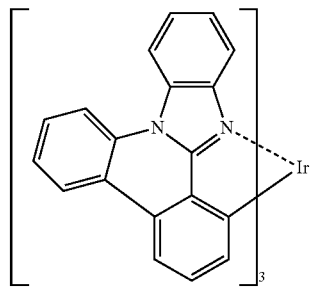
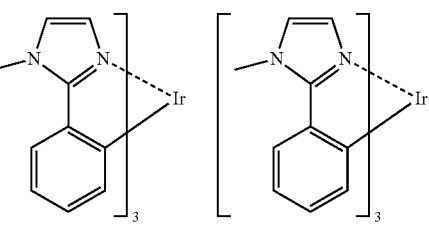
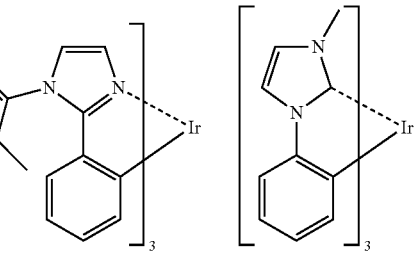
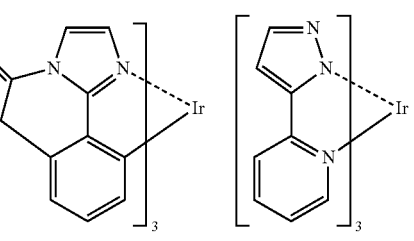
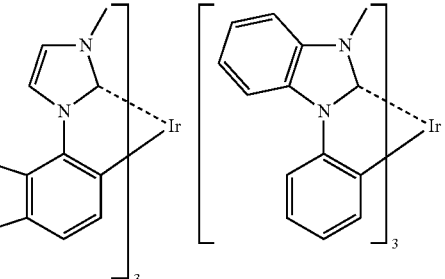

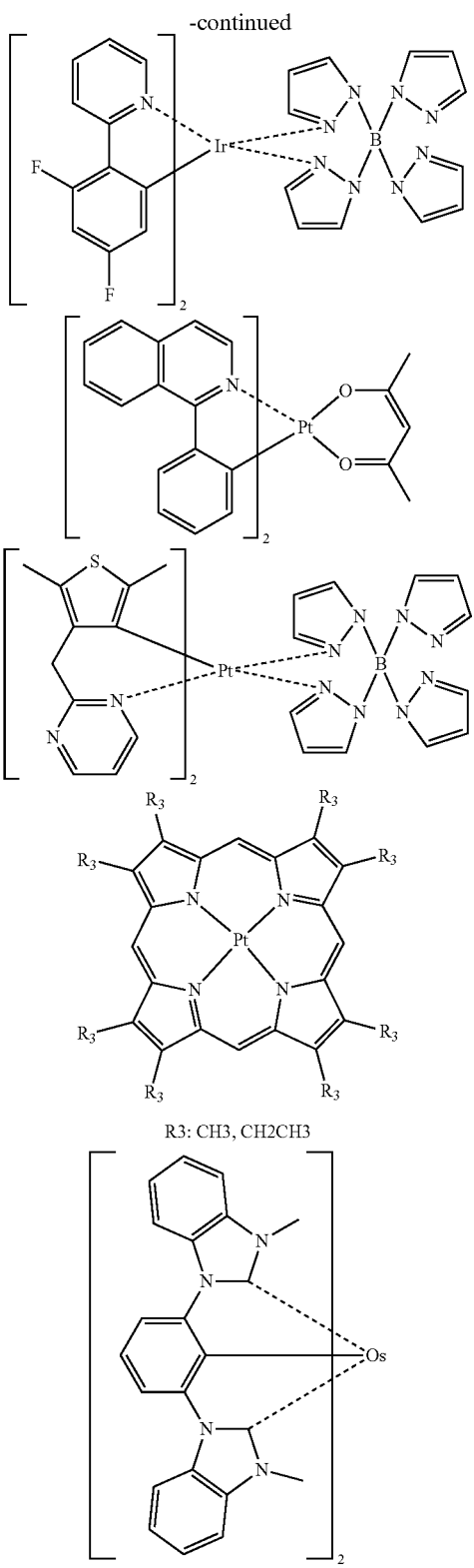

It is preferred that the content of the phosphorescent light-emitting dopant in the light-emitting layer fall within the range of 0.1 to 50 wt %, more preferably 1 to 30 wt %.

It is preferred to use, as a host material in the light-emitting layer, the carbazole compound represented by the general formula (1). However, when the carbazole compound is used in any of the organic layers other than the light-emitting layer, the material to be used in the light-emitting layer may be any other host material other than the carbazole compound, and the carbazole compound and any other host material may be used in combination. Further, a plurality of kinds of known host materials may be used in combination.

It is preferred to use, as a usable known host compound, a compound that has a hole-transporting ability or an electron-transporting ability, is capable of preventing luminescence from having a longer wavelength, and has a high glass transition temperature.

Such other host materials are known because they are mentioned in many patent literatures and the like, and hence may be chosen from those in the patent literatures and the like. Specific examples of the host material include, but not particularly limited to, an indole derivative, a carbazole derivative, an indolocarbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrin-based compound, an anthraquinodimethane derivative, an anthrone derivative, a diphenylquinone derivative, a thiopyran dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly(N-vinylcarbazole) derivative, an aniline-based copolymer, a thiophene oligomer, a polythiophene derivative, a polyphenylene derivative, a polyphenylenevinylene derivative, and a polyfluorene derivative.

—Injecting Layer—

The injecting layer refers to a layer formed between an electrode and an organic layer for the purpose of lowering a driving voltage and improving a light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

The carbazole compound represented by the general formula (1) is preferably used in the hole-blocking layer. However, when the carbazole compound is used in any other organic layer, a known material for a hole-blocking layer may be used. In addition, it is possible to use, as a material for the hole-blocking layer, any of materials for the electron-transporting layer to be described later as required.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

Any of materials for the hole-transporting layer to be described later can be used as a material for the electron-blocking layer as required. The thickness of the electron-blocking layer is preferably 3 to 100 nm, more preferably 5 to 30 nm.

—Exciton-Blocking Layer—

The exciton-blocking layer refers to a layer used for blocking excitons produced by the recombination of a hole and an electron in the light-emitting layer from diffusing in charge-transporting layers. The insertion of this layer enables effective confinement of the excitons in the light-emitting layer, thereby being able to improve the luminous efficiency of the device. The exciton-blocking layer may be inserted on any of the anode side and the cathode side of the adjacent light-emitting layer, and may also be inserted simultaneously on both sides.

As a material for the exciton-blocking layer, for example, there are given 1,3-dicarbazolylbenzene (mCP) and bis(2-methyl-8-quinolinolato)-4-phenylphenolatoaluminum (III) (BAlq).

—Hole-Transport Layer—

The hole-transporting layer is formed of a hole-transporting material having a function of transporting holes, and a single hole-transporting layer or a plurality of hole-transporting layers may be formed.

The hole-transporting material has any one of hole-injecting property, hole-transporting property, and electron-blocking property, and any of an organic compound and an inorganic compound may be used. It is preferred to use the carbazole compound represented by the general formula (1) in the hole-transporting layer. However, any compound selected from conventionally known compounds may be used. Examples of the known hole-transporting material that may be used include a triazole derivative, an oxadiazole derivative, an imidazole derivative, a polyarylalkane derivative, a pyrazoline derivative and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular weight oligomer, in particular, a thiophene oligomer. However, a triazole derivative, an oxadiazole derivative, an imidazole derivative, or an arylamine derivative is preferably used, and an arylamine derivative is more preferably used.

—Electron-Transport Layer—

The electron-transporting layer is formed of a material having a function of transporting electrons, and a single electron-transporting layer or a plurality of electron-transporting layers may be formed.

An electron-transporting material (which also serves as a hole-blocking material in some cases) has only to have a function of transferring electrons injected from the cathode into the light-emitting layer. The carbazole compound represented by the general formula (1) according to the present invention is preferably used in the electron-transporting layer. However, any compound selected from conventionally known compounds may be used. Examples thereof include a nitro-substituted fluorene derivative, a diphenylquinone derivative, a thiopyran dioxide derivative, a carbodiimide, a fluorenylidenemethane derivative, anthraquinodimethane and an anthrone derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative that has a quinoxaline ring known as an electron withdrawing group. Further, it is also possible to use a polymer material in which any of those materials is introduced in a polymer chain or is used as a polymer main chain.

Hereinafter, the present invention is described in more detail by way of Examples. It should be appreciated that the present invention is not limited to Examples below and may be carried out in various forms as long as the various forms do not deviate from the gist of the present invention.

The routes described below were used to synthesize a carbazole compound to be used as a material for a phosphorescent light-emitting device. It should be noted that the number of each compound corresponds to the number given to the exemplified compound.

EXAMPLE 1

Synthesis of compound (I)

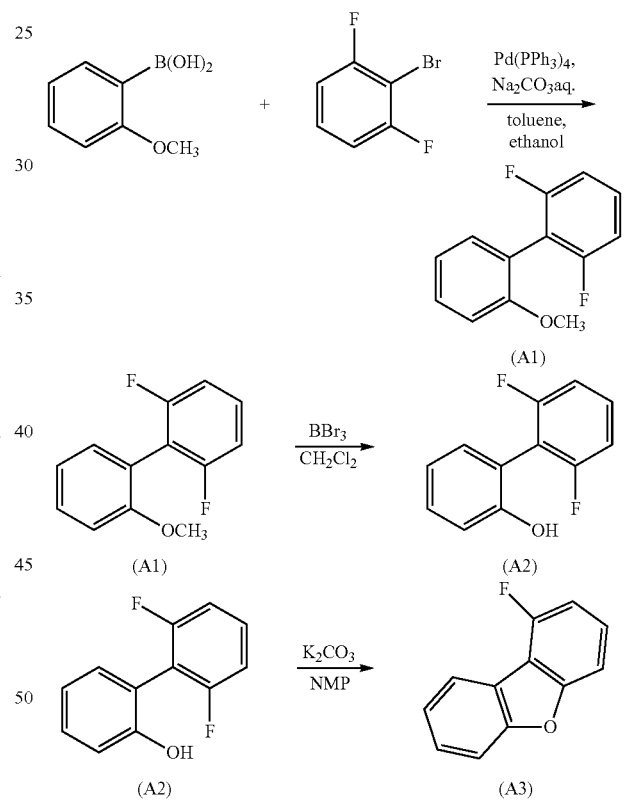

Under a nitrogen atmosphere, 18.84 g (0.124 mol) of 2-methoxyphenylboronic acid, 24.00 g (0.124 mol) of 1-bromo-2,6-difluorobenzene, 7.72 g (0.00496 mol) of tetrakis(triphenylphosphine)palladium (0), 600 ml of toluene, and 100 ml of ethanol were loaded, and then 200 ml of a 2 M aqueous solution of sodium hydroxide were added to the mixture while the mixture was stirred at room temperature. The resultant was stirred at 90° C. for 5 hr, and was then cooled to room temperature, followed by the washing of the organic layer with distilled water (300 ml×3). After the organic layer had been dried with anhydrous magnesium sulfate, magnesium sulfate was separated by filtration and then the solvent was distilled off under reduced pressure. The resultant residue was purified by silica gel column chromatography to provide 10.01 g (0.0455 mol, 38% yield) of an intermediate (A1) as a white solid.

Under a nitrogen atmosphere, 10.00 g (0.0454 mol) of the intermediate (A1) and 100 ml of dichloromethane were loaded, and then 20 ml of a solution of boron tribromide in dichloromethane were added to the mixture while the mixture was stirred at 0° C. The resultant was stirred at room temperature for 6 hr and then water was added thereto. The organic layer was washed with distilled water (30 ml×3). After the organic layer had been dried with anhydrous magnesium sulfate, magnesium sulfate was separated by filtration and then the solvent was distilled off under reduced pressure. The resultant residue was purified by silica gel column chromatography to provide 8.62 g (0.0418 mol, 92% yield) of an intermediate (A2) as a colorless liquid.

Under a nitrogen atmosphere, 8.62 g (0.0418 mol) of the intermediate (A2) and 230 ml of N-methyl-pyrrolidone were loaded, and then 11.56 g (0.0836 mol) of potassium carbonate were added to the mixture while the mixture was stirred at room temperature. The resultant was stirred at 180° C. for 3 hr. After that, the resultant was cooled to room temperature and then potassium carbonate was separated by filtration. 900 ml of distilled water were added to the filtrate and then the mixture was stirred at room temperature. After that, the precipitated solid was separated by filtration. The resultant solid was dissolved in dichloromethane and then the organic layer was washed with distilled water (30 ml×3). After the organic layer had been dried with anhydrous magnesium sulfate, magnesium sulfate was separated by filtration and then the solvent was distilled off under reduced pressure. The resultant residue was purified by silica gel column chromatography to provide 7.02 g (0.0377 mol, 90% yield) of an intermediate (A3) as a white solid.

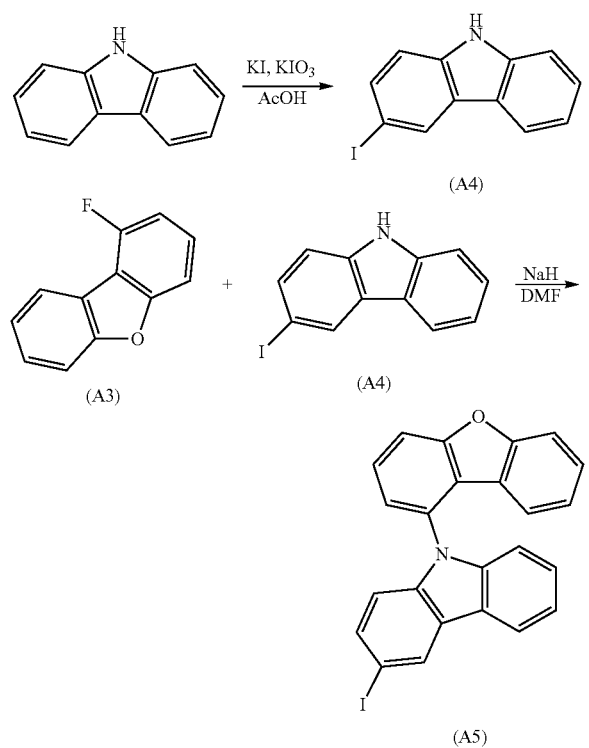

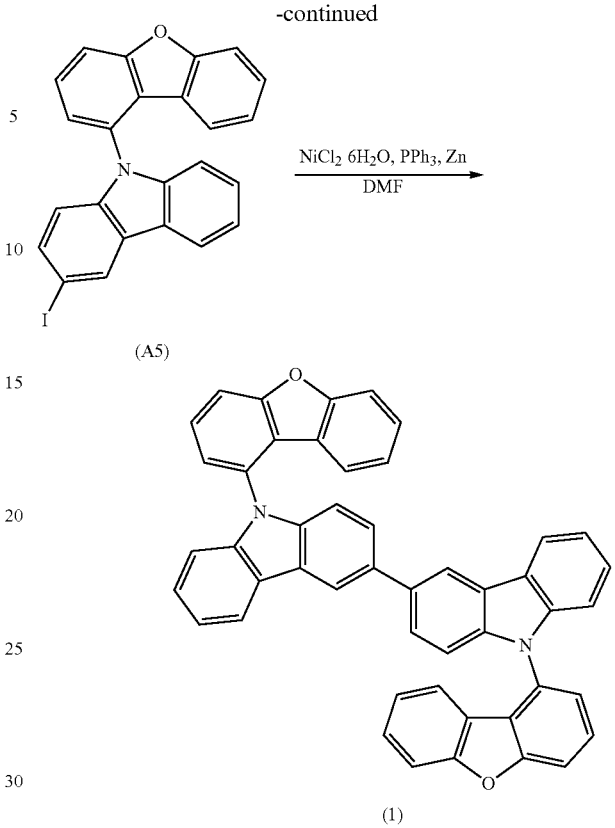

Under a nitrogen atmosphere, 35 g (0.209 mol) of carbazole and 300 ml of acetic acid were loaded, and then 24.24 g (0.146 mol) of potassium iodide and 31.24 g (0.146 mol) of potassium iodate were added to the mixture while the mixture was stirred at room temperature. The resultant was stirred at 80° C. for 2 hr, and was then cooled to room temperature. 300 ml of an aqueous solution of sodium hydrogen sulfite and 300 ml of tetrahydrofuran were added to the resultant, and then the mixture was stirred at room temperature. 300 ml of toluene were added to the mixture and then the organic layer was washed with distilled water (200 ml×2). After the organic layer had been dried with anhydrous magnesium sulfate, magnesium sulfate was separated by filtration and then the solvent was distilled off under reduced pressure. The resultant residue was purified by recrystallization to provide 20.75 g (0.0708 mol) of an intermediate (A4) as a white solid.

Under a nitrogen atmosphere, 3.03 g (0.0752 mol) of sodium hydride and 20 ml of dimethylformamide (DMF) were loaded, and then 20 ml of a DMF solution in which 20.00 g (0.0682 mol) of the intermediate (A4) had been dissolved were added to the mixture while the mixture was stirred at room temperature. The resultant was stirred at room temperature for 30 min, and then 20 ml of a DMF solution in which 7.00 g (0.0376 mol) of the intermediate (A3) had been dissolved were added thereto. The mixture was stirred at 120° C. for 7 hr, and was then cooled to room temperature. 300 ml of distilled water were added to the mixture and then the whole was stirred at room temperature. The precipitated solid was separated by filtration. The resultant solid was dissolved in tetrahydrofuran and then 200 ml of distilled water were added to the solution. The mixture was extracted with toluene (100 ml×3), and then the organic layer was dried with anhydrous magnesium sulfate. After that, magnesium sulfate was separated by filtration and then the solvent was distilled off under reduced pressure. The resultant residue was purified by silica gel column chromatography to provide 16.74 g (0.0364 mol, 97% yield) of an intermediate (A5) as a white solid.

Under a nitrogen atmosphere, 4.16 g (0.0152 mol) of nickel (II) chloride hexahydrate, 16.34 g (0.0623 mol) of triphenylphosphine, and 50 ml of dimethylformamide were loaded, followed by deaeration. 1.29 g (0.0198 mol) of zinc were added to the mixture and then the whole was stirred at 60° C. for 20 min. 50 ml of a dimethylformamide solution in which 5.84 g (0.0127 mol) of the intermediate (A5) had been dissolved were added to the resultant, and then the mixture was stirred at 90° C. for 4 hr. The reaction solution was cooled to room temperature, and was then poured into 300 ml of water, followed by stirring at room temperature for 2 hr. The precipitate was separated by filtration, and was then dissolved in tetrahydrofuran, followed by the addition of 150 ml of water to the solution. The mixture was extracted with toluene (50 ml×3), and then the organic layer was dried with anhydrous magnesium sulfate. After that, magnesium sulfate was separated by filtration and then the solvent was distilled off under reduced pressure. The resultant residue was purified by silica gel column chromatography and recrystallization to provide 0.17 g (0.000256 mol, 2% yield) of a compound (I) as a white solid.

Figure 2:
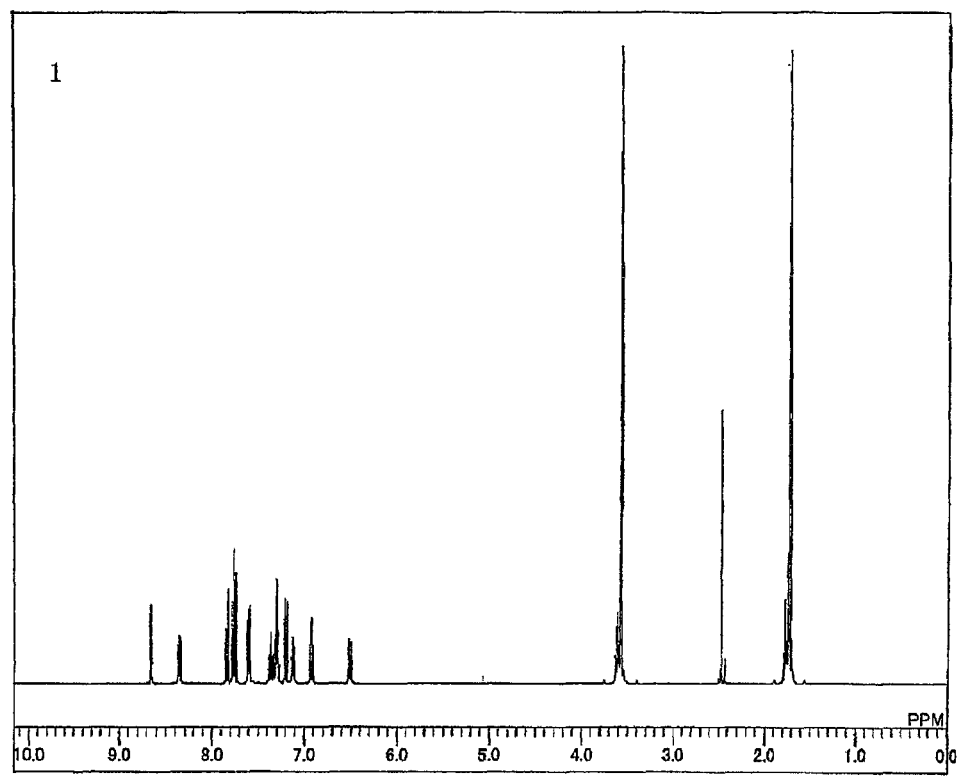
FIG. 2 shows a $^1$H-NMR chart of a carbazole compound (I).

The APCI-TOFMS of the compound showed an [M+1] peak at an m/z of 665. FIG. 2 shows the results of its $^1$H-NMR measurement (measurement solvent: THF-d8).

EXAMPLE 2

Synthesis of Compound (40)

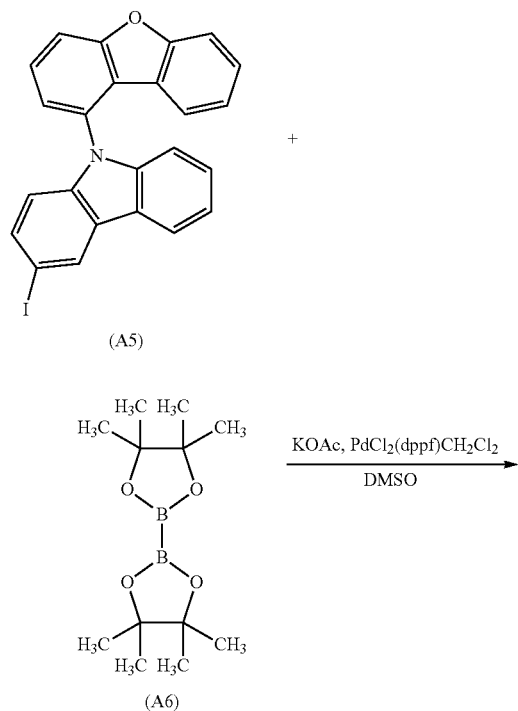

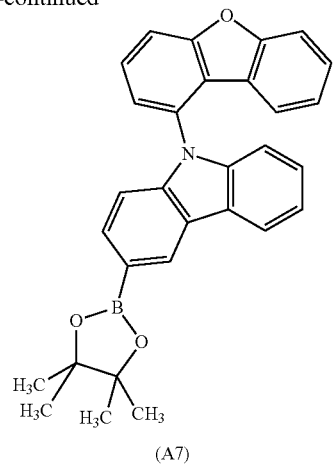

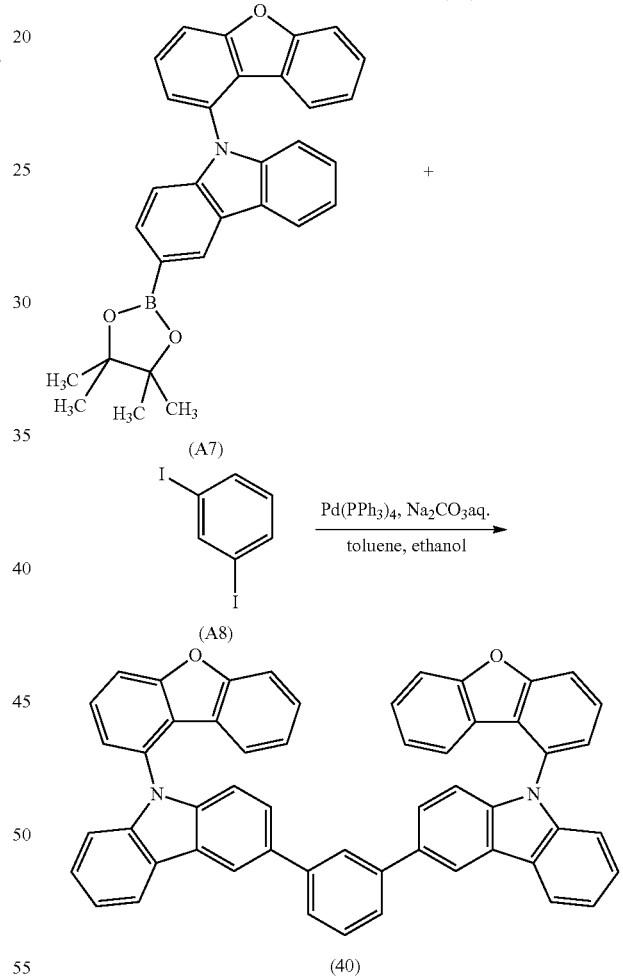

Under a nitrogen atmosphere, 18.00 g (0.0392 mol) of the intermediate (A5), 11.94 g (0.0470 mol) of bispinacolatodiboron, 11.54 g (0.1176 mol) of potassium acetate, and 200 ml of dimethyl sulfoxide (DMSO) were loaded, and then the mixture was stirred at 60° C. for 30 min. After that, 0.96 g (0.00118 mol) of a 1,1'-bis(diphenylphosphino)ferrocene-palladium(II)dichloride-dichloromethane complex was added to the mixture, and then the whole was stirred at 80° C. for 6 hr. After that, the reaction solution was cooled to room temperature. The cooled reaction solution was poured into water and then the mixture was stirred at room temperature for 6 hr. After that, the precipitated solid was separated by filtration. The resultant solid was purified by silica gel column chromatography to provide 9.99 g (0.0217 mol, 55% yield) of an intermediate (A7) as a white solid.

Under a nitrogen atmosphere, 9.50 g (0.0207 mol) of the intermediate (A7), 3.10 g (0.0094 mol) of 1,3-diiodobenzene, 0.58 g (0.000376 mol) of tetrakis(triphenylphosphine) palladium, 300 ml of toluene, and 50 ml of ethanol were loaded, and then 15 ml of a 2 M aqueous solution of sodium hydroxide were added to the mixture while the mixture was stirred at room temperature. After that, the resultant was stirred at 70° C. for 9 hr. The reaction solution was cooled to room temperature and then the organic layer was washed with distilled water (100 ml×3). After the organic layer had been dried with anhydrous magnesium sulfate, magnesium sulfate was separated by filtration and then the solvent was distilled off under reduced pressure. The resultant residue was purified by silica gel column chromatography and recrystallization to provide 2.08 g (0.00281 mol, 30% yield) of a compound (40) as a white solid.

Figure 3:
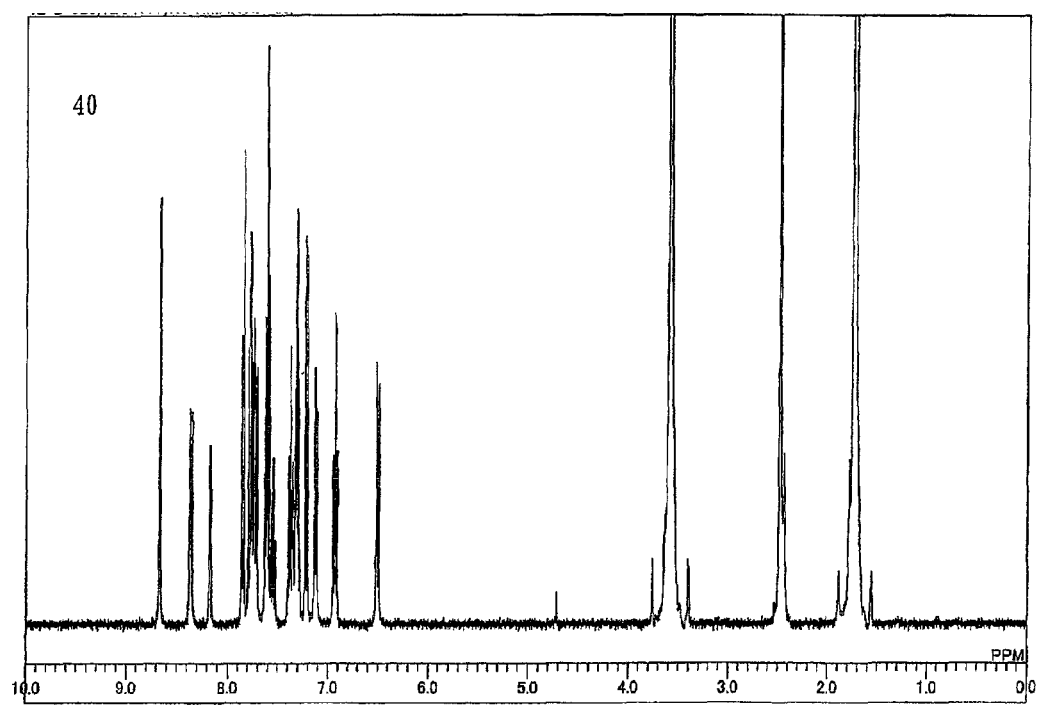
FIG. 3 shows a $^1$H-NMR chart of a carbazole compound (40).

The APCI-TOFMS of the compound showed an [M+1] peak at an m/z of 741. FIG. 3 shows the results of its $^1$H-NMR measurement (measurement solvent: THF-d8).

EXAMPLE 3

Each thin film was laminated by a vacuum deposition method at a degree of vacuum of $4.0 \times 10^{-5}$ Pa on a glass substrate on which an anode formed of an ITO substrate having a thickness of 110 nm had been formed. First, CuPC was formed on ITO so as to have a thickness of 20 nm. Next, NPB was formed thereon so as to serve as a hole-transport layer having a thickness of 20 nm. Next, the compound (I) as a host material and Ir(ppy)$_3$ as a dopant were co-deposited from different deposition sources onto the hole-transport layer to form a light-emitting layer having a thickness of 30 nm. The concentration of Ir(ppy)$_3$ in this case was 10 wt %. Next, Alq3 was formed thereon so as to serve as an electron-transport layer having a thickness of 40 nm. Further, lithium fluoride (LiF) was formed on the electron-transport layer so as to serve as an electron-injecting layer having a thickness of 1 nm. Finally, aluminum (Al) was formed on the electron-injecting layer so as to serve as an electrode having a thickness of 70 nm. Thus, an organic EL device was produced.

An external power source was connected to the resultant organic EL device to apply a DC voltage to the device. As a result, it was confirmed that the device had such light-emitting characteristics as shown in Table 1. The columns "luminance", "voltage", and "luminous efficiency" in Table 1 show values obtained when the device was driven at 20 mA/cm$^2$. It was found that the local maximum wavelength of the emission spectrum of the device was 540 nm and hence light emission from Ir(ppy)$_3$ was obtained.

EXAMPLES 4 to 11

Compounds 8, 11, 17, 18, 20, and 31 were synthesized in the same manner as in Example 1, and organic EL devices were each produced in the same manner as in Example 3 except that the compound 8, 11, 17, 18, 20, 31, or 40 was used instead of the compound 1 as the host material for the light-emitting layer in Example 3. It was found that the local maximum wavelength of the emission spectrum of each of the devices was 540 nm and hence light emission from Ir(ppy)$_3$ was obtained.

EXAMPLES 12 and 13

Comparisons

Organic EL devices were each produced in the same manner as in Example 3 except that CBP or a compound H-1 was used as the host material for the light-emitting layer in Example 3. It was identified that the local maximum wavelength of the emission spectrum of the device was 535 nm (Example 12) or 530 nm (Example 13) and hence light emission from Ir(ppy)$_3$ was obtained.

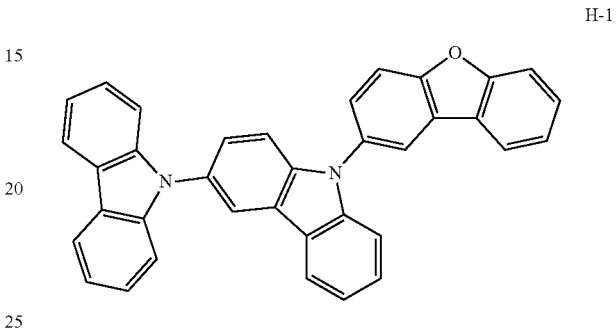

H-1

TABLE 1

| Example | Host compound | Luminance (cd/m$^2$) | Voltage (V) | Visual luminous efficiency (lm/W) |
|---|---|---|---|---|
| 3 | 1 | 2450 | 9.0 | 4.3 |
| 4 | 6 | 1850 | 9.1 | 3.2 |
| 5 | 8 | 2220 | 10.2 | 3.4 |
| 6 | 11 | 2090 | 9.5 | 3.5 |
| 7 | 17 | 2360 | 9.2 | 4.0 |
| 8 | 18 | 2130 | 9.2 | 3.6 |
| 9 | 20 | 2160 | 8.9 | 3.8 |
| 10 | 31 | 2400 | 9.1 | 4.1 |
| 11 | 40 | 2530 | 8.9 | 4.5 |
| 12 | CBP | 1120 | 8.7 | 2.0 |
| 13 | H-1 | 1320 | 9.3 | 2.2 |

Example 3 is improved in initial characteristics as compared with Examples 12 and 13 (comparisons). The foregoing shows that the use of a compound, which has carbazole at the 1-position of dibenzothiophene or dibenzofuran and has a specific substituent at any one of the 2- to 7-positions of carbazole, in an organic EL device improves the characteristics of the organic EL device. The characteristics of the EL devices of Examples 4 to 11 are similarly good, which also shows the superiority of the carbazole compound represented by the general formula (1).

Industrial Applicability

The carbazole compound represented by the general formula (1) to be used in the organic electroluminescent device of the present invention may enable the fine adjustment of hole and electron mobilities, and the control of various energy values, i.e., an ionization potential (IP), an electron affinity (EA), and a triplet energy (T1) because 2 to 4 skeletons in each of which the N-position of carbazole is bonded to the 1-position of dibenzothiophene or dibenzofuran are linked at the 3-position of carbazole. In addition, it may be possible to improve the stability of the carbazole compound in each of active states, i.e., oxidation, reduction, and excitation, and at the same time, the compound has good amorphous property. As a result of the foregoing, the compound can realize an organic EL device having a long driving lifetime and high durability.

The organic EL device according to the present invention has light-emitting characteristics, driving lifetime, and durability at practically satisfactory levels. Thus, the organic EL device has a large technical value in applications to flat panel displays (display devices for portable phones, in-vehicle display devices, display devices for OA computers, televisions, and the like), light sources utilizing characteristics of planar light emitters (light sources in lighting equipment and copying machines and backlight sources in liquid crystal displays and instruments), sign boards, sign lamps, and the like.

The invention claimed is:

1. An organic electroluminescent device, comprising:
a substrate;
an anode;
an organic layer; and
a cathode,
the anode, the organic layer, and the cathode being laminated on the substrate,
wherein the organic layer comprises at least one layer selected from the group consisting of a light-emitting layer, a hole-transporting layer, an electron-transporting layer, and a hole-blocking layer, the at least one layer containing a carbazole compound represented by the general formula (1):

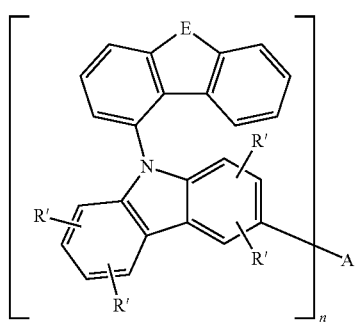

(1)

where:
A represents an n-valent aromatic hydrocarbon group having 6 to 18 carbon atoms, an n-valent aromatic heterocyclic group having 3 to 17 carbon atoms, or an n-valent group obtained by linking 2 to 4 aromatic rings each selected from an aromatic hydrocarbon ring having 6 to 18 carbon atoms and an aromatic heterocyclic ring having 3 to 17 carbon atoms, and the aromatic hydrocarbon group, the aromatic heterocyclic group, the aromatic hydrocarbon ring, and the aromatic heterocyclic ring may each have a substituent;
R's represents hydrogen;
E represents oxygen or sulfur; and
n represents an integer of 2 to 4.

2. An organic electroluminescent device according to claim 1, wherein A in the general formula (1) represents any one of an n-valent aromatic heterocyclic group having 3 to 17 carbon atoms, and an n-valent group obtained by linking 2 to 4 aromatic rings, each of which is an aromatic heterocyclic ring having 3 to 17 carbon atoms.

3. An organic electroluminescent device according to claim 2, wherein A represents any one of the n-valent aromatic heterocyclic group, and the n-valent group obtained by linking 2 to 4 aromatic rings, each of which is an aromatic heterocyclic ring having 3 to 17 carbon atoms, and n represents 2 or 3.

4. An organic electroluminescent device according to claim 1, wherein the layer containing the carbazole compound represented by the general formula (1) comprises a light-emitting layer containing a phosphorescent light-emitting dopant.

5. An organic electroluminescent device according to claim 1, wherein the carbazole compound is selected from:

17

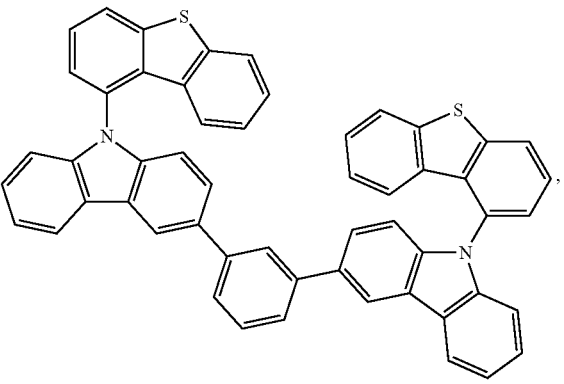

18

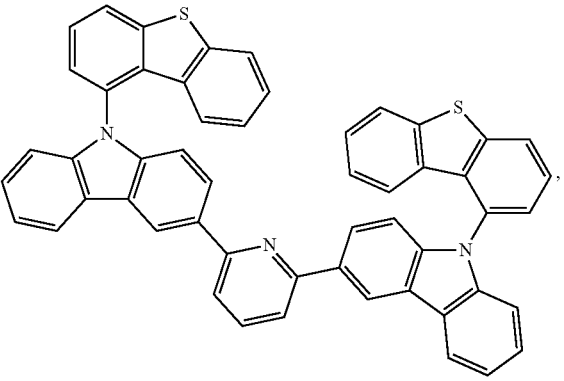

20

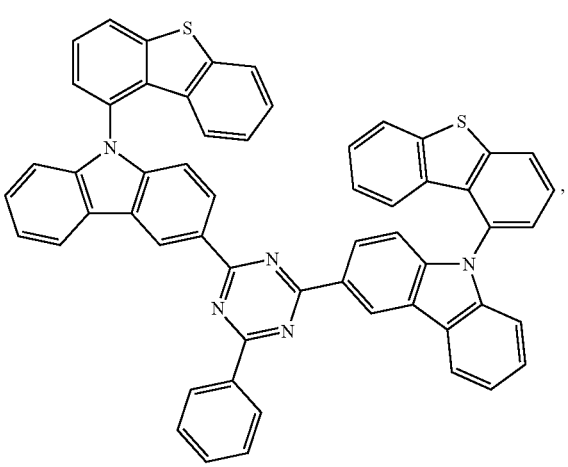

-continued
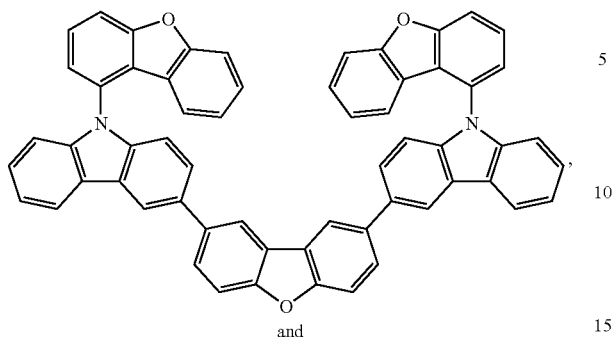
and
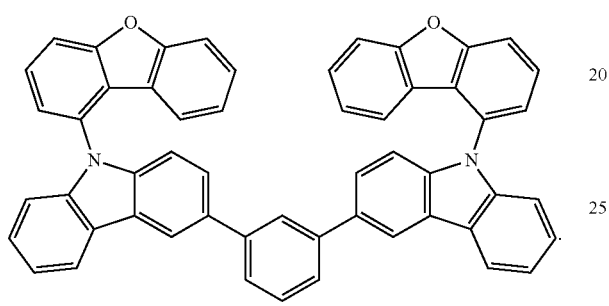
* * * * *